US010603429B2

(12) United States Patent
Dantsker

(10) Patent No.: US 10,603,429 B2
(45) Date of Patent: Mar. 31, 2020

(54) SUBCUTANEOUS INJECTION SYSTEM WITH ADHESIVE INJECTION SITE INDICATOR

(71) Applicant: Capsule Technologies, Inc., San Diego, CA (US)

(72) Inventor: Eugene Dantsker, San Diego, CA (US)

(73) Assignee: CAPSULE TECHNOLOGIES, INC., San Diego, CA (US)

( * ) Notice: Subject to any disclaimer, the term of this patent is extended or adjusted under 35 U.S.C. 154(b) by 845 days.

(21) Appl. No.: 14/697,483

(22) Filed: Apr. 27, 2015

(65) Prior Publication Data

US 2016/0310663 A1    Oct. 27, 2016

(51) Int. Cl.
*A61M 5/142* (2006.01)
*A61M 5/172* (2006.01)
(Continued)

(52) U.S. Cl.
CPC ........ *A61M 5/14248* (2013.01); *A61M 5/172* (2013.01); *A61M 5/1723* (2013.01); *A61M 5/20* (2013.01); *A61M 5/24* (2013.01); *A61M 5/31571* (2013.01); *A61M 5/427* (2013.01); *G06F 19/3481* (2013.01); *H04W 4/80* (2018.02); *A61M 2005/1726* (2013.01); *A61M 2205/13* (2013.01); *A61M 2205/33* (2013.01);
(Continued)

(58) Field of Classification Search
CPC ........ A61B 5/6833; A61M 2205/3569; A61M 2205/6009; A61M 5/427; A61M 2205/276; G06F 19/3468; A61F 2013/00417
See application file for complete search history.

(56) References Cited

U.S. PATENT DOCUMENTS 8,235,949 B2    8/2012    Hack et al.
8,285,328 B2    10/2012    Caffey et al.
(Continued)

FOREIGN PATENT DOCUMENTS

WO    2012171885    12/2012
WO    2013070705    5/2013
(Continued)

OTHER PUBLICATIONS

International Search Report and Written Opinion—PCT/US2016/028322—ISA/EPO—dated Jul. 26, 2016.

*Primary Examiner* — Emily L Schmidt
(74) *Attorney, Agent, or Firm* — Kilpatrick Townsend & Stockton LLP

(57) ABSTRACT

Described herein are subcutaneous medication delivery applicators and adhesive patches with one or more openings in the patches that designate one or more desired injection sites for subcutaneous injection of a medication. The medication delivery applicator and the adhesive patch may both include circuitry and wireless short-range communications interfaces that allow for the two devices to communicate with one another in order to determine if they are pre-associated in some manner, such as would be the case if both devices were packaged in the same injection kit. The medication delivery applicator may have some form of safety interlock that is only disengaged by the circuitry upon verifying that the two devices are pre-associated in some manner. Various other implementations are described as well.

30 Claims, 9 Drawing Sheets

(51) Int. Cl.
 *G06F 19/00* (2018.01)
 *A61M 5/24* (2006.01)
 *A61M 5/42* (2006.01)
 *A61M 5/315* (2006.01)
 *A61M 5/20* (2006.01)
 *H04W 4/80* (2018.01)

(52) U.S. Cl.
 CPC . *A61M 2205/35* (2013.01); *A61M 2205/3546* (2013.01); *A61M 2205/3553* (2013.01); *A61M 2205/3569* (2013.01); *A61M 2205/3576* (2013.01); *A61M 2205/3584* (2013.01); *A61M 2205/52* (2013.01); *A61M 2205/581* (2013.01); *A61M 2205/60* (2013.01); *A61M 2210/04* (2013.01)

(56) References Cited

U.S. PATENT DOCUMENTS

| | | |
|---|---|---|
| 8,696,629 B2 | 4/2014 | Yodfat et al. |
| 8,764,653 B2 | 7/2014 | Kaminska et al. |
| 8,778,393 B2 | 7/2014 | Palmer et al. |
| 2001/0037104 A1* | 11/2001 | Zhang .............. A61K 9/0004 604/502 |
| 2009/0043253 A1 | 2/2009 | Podaima |
| 2009/0312706 A1 | 12/2009 | Shantha et al. |
| 2011/0118694 A1* | 5/2011 | Yodfat ............. G06F 19/3456 604/500 |
| 2013/0123719 A1 | 5/2013 | Mao et al. |
| 2014/0012102 A1 | 1/2014 | Das et al. |
| 2014/0121557 A1 | 5/2014 | Gannon et al. |
| 2014/0128842 A1 | 5/2014 | Deberadine |
| 2014/0247109 A1* | 9/2014 | Curry ................ G06Q 10/00 340/5.1 |
| 2014/0275932 A1 | 9/2014 | Zadig |
| 2014/0330243 A1 | 11/2014 | Kietzmann et al. |

FOREIGN PATENT DOCUMENTS

| | | | |
|---|---|---|---|
| WO | WO 2013070715 A1 * | 5/2013 | ........ A61M 37/0015 |
| WO | 2014116816 | 7/2014 | |

* cited by examiner

SUBCUTANEOUS INJECTION SYSTEM WITH ADHESIVE INJECTION SITE INDICATOR

TECHNICAL FIELD

This disclosure relates generally to the field of injectable medication systems and, more particularly, to the field of systems for providing self-administerable injectable medications and that include functionality for ensuring that guidelines for proper medication use are followed.

DESCRIPTION OF THE RELATED TECHNOLOGY

There are a number of medications that are prescribed for patients today that require subcutaneous injection and that may need to be injected on a regular basis that would make it prohibitively expensive or impractical to have a physician or nurse perform the injections. For example, diabetics may need to routinely inject insulin to ward off complications from diabetes. Other examples of such medications may include, but are not limited to, steroids, HIV medications, arthritis medications, fertility treatment medications, etc.

SUMMARY

The systems, methods and devices of this disclosure each have several innovative aspects, no single one of which is solely responsible for the desirable attributes disclosed herein. Included among these aspects are at least the following implementations, although further implementations may be set forth in the detailed description or may be evident from the discussion provided herein.

In some implementations, a system may be provided that includes an adhesive patch, a subcutaneous medication delivery applicator (SMDA), and control logic. The adhesive patch may include a flexible substrate having an adhesive backing for adhering the flexible substrate to a person's skin, as well as one or more openings, each opening indicating a post-adhesion, designated injection site for subcutaneous medication delivery when the adhesive patch is adhered to the person's skin. The adhesive patch may also include a first short-range wireless communications interface and a first portion of the control logic. The SMDA may include a mechanism configured to subcutaneously deliver an amount of medication through the person's skin, a second short-range wireless communications interface configured to receive and transmit information from and to, respectively, at least the first short-range wireless communications interface, a safety interlock that prevents the mechanism from dispensing the medication when the safety interlock is engaged and that allows the mechanism to dispense the medication when disengaged, and a second portion of the control logic. The control logic may be operatively connected with the first short-range wireless communications interface via the first portion and with the second short-range wireless communications interface and the safety interlock via the second portion. The first portion of the control logic and the second portion of the control logic may be configured to communicate with each other via the first short-range wireless communications interface and the second short-range wireless communications interface, respectively. The control logic may be configured to determine whether subcutaneous injection of the medication is authorized at a first time based, at least in part, on information transmitted via the first short-range wireless communications interface, the second short-range wireless communications interface, or the first short-range wireless communications interface and the second short-range wireless communications interface, and to cause the safety interlock to disengage responsive to a determination that the subcutaneous injection of the medication is authorized.

In some such implementations, the SMDA may be a syringe, an autoinjector syringe, or a needleless jet-injector.

In some implementations, the adhesive patch may be configured to short-circuit itself upon removal from the person's skin.

In some implementations, the one or more openings in the flexible substrate may include a plurality of openings, each opening indicated by a different distinguishing characteristic, such as different colored borders around each opening, different shapes for each opening, different numbers for each opening, different letters for each opening, different symbols for each opening, or combinations thereof.

In some implementations, the one or more openings in the flexible substrate may include a plurality of openings and the adhesive patch may further include a plurality of switchable visual indicators. Each of the visual indicators may be positioned adjacent to a different one of the openings, and the control logic may be configured to cause one or more of the switchable visual indicators to switch to a different state to indicate one or more of the post-adhesion, designated injection sites responsive to a determination that the subcutaneous injection of the medication is authorized.

In some implementations of the system, the control logic may be further configured to determine that the subcutaneous injection of the medication is authorized based, at least in part, on a determination that the information indicates that the adhesive patch is pre-associated with the SMDA.

In some such implementations, the control logic may be further configured to determine, based at least in part on the information, a most recent time prior to the first time that subcutaneous delivery of the medication was performed; determine whether the amount of time between the most recent time and the first time is more than a first threshold amount of time; and determine that the subcutaneous injection of the medication is authorized at the first time based, at least further in part, on a determination that the amount of time between the most recent time and the first time is more than the first threshold amount of time.

In some further such implementations, the most recent time when the subcutaneous delivery was performed may be determined based on a most recent occurrence or occurrences of one or more events, such as a previous instance in which the safety interlock of the SMDA was disengaged, a previous instance in which the safety interlock of another SMDA that was previously in communication with the control logic was disengaged, an indication from the SMDA that a volume of medication contained within the SMDA decreased, an indication from another SMDA that was previously in communication with the control logic that a volume of medication contained within the other SMDA decreased, an indication from a sensor located in the adhesive patch that the person's flesh in the vicinity of the adhesive patch changed electrical characteristics consistent with insertion of a needle into the person's flesh at that location, an indication from a sensor located in another adhesive patch that was previously in communication with the control logic that the person's flesh in the vicinity of the other adhesive patch changed electrical characteristics consistent with insertion of a needle into the person's flesh at that location, an indication from a sensor located in the SMDA that indicates that a hypodermic needle included in the SMDA has experienced a change in electrical characteristics consistent with contact of the hypodermic needle with the person's skin, and/or an indication from a sensor located in another SMDA that was previously in communication with the control logic that indicates that a hypodermic needle included in the other SMDA experienced a change in electrical characteristics consistent with contact of the hypodermic needle with the person's skin.

In some implementations of the system, the adhesive patch may further include a transdermal medication dispenser, the first portion of the control logic may also be operatively connected with the transdermal medication dispenser, and the control logic may be configured to adjust a rate of transdermal medication dispensation from the transdermal medication dispenser based, at least in part, on a determination that the subcutaneous injection of the medication is authorized.

In some implementations of the system, the system may further include a mobile communications device with a third short-range wireless communications interface and a first long-range wireless communications interface. In such implementations, the control logic may be further operatively connected with the third short-range wireless communications interface and the first long-range wireless communications interface and may further include a third portion that is included in the mobile communications device and that is configured to communicate with one or both of the first portion and the second portion via the third short-range wireless communications interface. The control logic may be further configured to determine whether the subcutaneous injection of the medication is authorized at the first time based, at least further in part, on further information transmitted via the third short-range wireless communications interface or the first long-range wireless communications interface.

In some such implementations, the adhesive patch may further include one or more sensors configured to obtain physiological data regarding the person, and the control logic may be configured to determine that, at the first time, the physiological data indicates that the person is experiencing a medical condition that presents an elevated risk were the subcutaneous injection of the medication to be authorized, and initiate, responsive to the determination that the physiological data indicates that the person is experiencing the medical condition that presents the elevated risk were the subcutaneous injection of the medication to be authorized, communications between the mobile communications device and a remote assistance center using the first long-range wireless communications interface.

In some further such implementations, the one or more sensors may include one or more sensors such as a body temperature sensor, an electrocardiogram sensor, an oxygen saturation sensor, a bioimpedance sensor, an electroencephalography sensor, an electromyographic sensor, a blood glucose sensor, a heart rate sensor, a heart rate variability sensor, a respiratory rate sensor, or combinations thereof.

In some implementations of the system, the adhesive patch may further include an alert mechanism such as a haptic feedback device and/or an audio speaker, and the control logic may be further configured to determine a time at which the medication is to be administered and cause the alert mechanism to activate responsive to determining that the medication is to be administered to indicate that the medication is to be administered at that time.

In some implementations of the system, the control logic may be further configured to track usage of the SMDA over time and store information regarding the usage of the SMDA in a memory.

In some such implementations, the system may further include a mobile communications device with a third short-range wireless communications interface and a first long-range wireless communications interface, and the control logic may be further operatively connected with the third short-range wireless communications interface and the first long-range wireless communications interface. The control logic may also further include a third portion that is included in the mobile communications device and that is configured to communicate with one or both of the first portion and the second portion via the third short-range wireless communications interface. The control logic may also be further configured to transmit the information regarding the usage of the SMDA to a remote storage via the first long-range wireless communications interface.

In some implementations of the system, the system may further include one or more additional SMDAs, each of which may include another second short-range wireless communications interface configured to receive and transmit information from and to, respectively, at least the first short-range wireless communications interface.

In some implementations of the system, the system may further include one or more additional adhesive patches, and each additional adhesive patch may also include another first short-range wireless communications interface configured to receive and transmit information from and to, respectively, at least the second short-range wireless communications interface.

In some implementations, an adhesive patch may be provided. The adhesive patch may include a flexible substrate having an adhesive backing for adhering the flexible substrate to a person's skin. The flexible substrate may have one or more openings, each opening indicating a post-adhesion, designated injection site for subcutaneous medication delivery when the adhesive patch is adhered to the person's skin. The adhesive patch may also include a first short-range wireless communications interface and first control logic operatively connected with the first short-range wireless communications interface. The first control logic may be configured to communicate with second control logic of a first subcutaneous medication delivery applicator (SMDA) via the first short-range wireless communications interface, determine whether subcutaneous injection of a medication associated with the first SMDA is authorized at a first time based, at least in part, on information received via the first short-range wireless communications interface, and send a first authorization signal to the first SMDA via the first short-range wireless communications interface responsive to a determination that the subcutaneous injection of the medication is authorized.

In some implementations of the adhesive patch, the one or more openings in the flexible substrate may include a plurality of openings, the adhesive patch may further include a plurality of switchable visual indicators, and each of the visual indicators may be positioned adjacent to a different one of the openings. The first control logic may be configured to cause one or more of the switchable visual indicators to switch to a different state to indicate one or more of the post-adhesion, designated injection sites responsive to a determination that the subcutaneous injection of the medication is authorized.

In some implementations of the adhesive patch, the one or more openings in the flexible substrate may include a plurality of openings, each opening indicated by a different distinguishing characteristic such as different colored borders around each opening, different shapes for each opening, different numbers for each opening, different letters for each opening, different symbols for each opening, or combinations thereof.

In some implementations of the adhesive patch, the first control logic may be further configured to determine that the subcutaneous injection of the medication is authorized based, at least in part, on a determination that the information indicates that the adhesive patch is pre-associated with the first SMDA.

In some such implementations of the adhesive patch, the first control logic may be further configured to determine, based at least in part on the information, the most recent time prior to the first time that subcutaneous delivery of the medication was performed, determine whether the amount of time between the most recent time and the first time is more than a first threshold amount of time, and determine that the subcutaneous injection of the medication is authorized at the first time based, at least further in part, on a determination that the amount of time between the most recent time and the first time is more than the first threshold amount of time.

In some implementations of the adhesive patch, the adhesive patch may further include a transdermal medication dispenser, the first control logic may also be operatively connected with the transdermal medication dispenser, and the first control logic may be configured to adjust a rate of transdermal medication dispensation from the transdermal medication dispenser based, at least in part, on a determination that the subcutaneous injection of the medication is authorized.

In some implementations of the adhesive patch, the first control logic may be further configured to store information that allows the first control logic to determine that a plurality of different SMDAs, including the first SMDA, are each pre-associated with the adhesive patch, and send a corresponding authorization signal to any of the SMDAs based, at least in part, on information received from that respective SMDA via the first short-range wireless communications interface when the information received from that SMDA indicates that that SMDA is pre-associated with the adhesive patch, wherein the corresponding authorization signal is the first authorization signal when the information received from one of the SMDAs indicates that the SMDA is the first SMDA.

In some such implementations of the adhesive patch, the information that allows the first control logic to determine that the plurality of different SMDAs, including the first SMDA, are pre-associated with the adhesive patch may include information identifying SMDAs from at least two different medication manufacturers or at least two different SMDA manufacturers.

In some additional implementations of the adhesive patch, the first control logic may be further configured to store information for each SMDA or each medication associated with each SMDA indicating the most recent time that medication or that SMDA was used, determine, prior to sending the corresponding authorization signal for any of the SMDAs, whether the amount of time between the most recent time that that medication or that SMDA was used and a current time is more than a threshold amount of time associated with that medication or that SMDA, and determine that the subcutaneous injection of that medication or the medication associated with that SMDA is authorized based, at least further in part, on a determination that the amount of time between the most recent time that that medication or that SMDA was used and the current time is more than the threshold amount of time associated with that medication or that SMDA.

In some implementation, a method may be provided. The method may include providing an adhesive patch and a subcutaneous medication delivery applicator (SMDA). The adhesive patch may include a flexible substrate having an adhesive backing for adhering the flexible substrate to a person's skin, the flexible substrate having one or more openings, each opening indicating a post-adhesion, designated injection site for subcutaneous medication delivery when the adhesive patch is adhered to the person's skin, and a first short-range wireless communications interface. The SMDA may include a mechanism configured to subcutaneously deliver an amount of medication through the person's skin, a second short-range wireless communications interface configured to receive and transmit information from and to, respectively, at least the first short-range wireless communications interface, and a safety interlock that prevents the mechanism from dispensing the medication when the safety interlock is engaged and that allows the mechanism to dispense the medication when disengaged. The adhesive patch and the SMDA each may include a portion of a control logic and may be configured to communicate with each other via the first short-range wireless communications interface and the second short-range wireless communications interface. The method may also include determining, by the control logic, whether subcutaneous injection of the medication is authorized at a first time based, at least in part, on information transmitted via the first short-range wireless communications interface, the second short-range wireless communications interface, or the first short-range wireless communications interface and the second short-range wireless communications interface, and causing, by the control logic, the safety interlock to disengage responsive to a determination that the subcutaneous injection of the medication is authorized.

In some implementations of the method, the one or more openings in the flexible substrate of the adhesive patch may include a plurality of openings, the adhesive patch may further include a plurality of switchable visual indicators, and each of the visual indicators may be positioned adjacent to a different one of the openings. The method may further include causing, by the control logic, one or more of the switchable visual indicators to switch to a different state to indicate one or more of the post-adhesion, designated injection sites responsive to a determination that the subcutaneous injection of the medication is authorized.

In some implementations of the method, the method may further include determining, by the control logic, that the subcutaneous injection of the medication is authorized based, at least in part, on a determination that the information indicates that the adhesive patch is pre-associated with the SMDA.

In some implementations of the method, the method may further include determining, by the control logic and based at least in part on the information, the most recent time prior to the first time that subcutaneous delivery of the medication was performed; determining, by the control logic, whether the amount of time between the most recent time and the first time is more than a first threshold amount of time; and determining, by the control logic, that the subcutaneous injection of the medication is authorized at the first time based, at least further in part, on a determination that the amount of time between the most recent time and the first time is more than the first threshold amount of time.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

Like reference numbers and designations in the various drawings indicate like elements. Additionally, a convention has been adopted herein where components that are similar between different drawings are referred to using the same last two digits of their corresponding reference numbers. In such situations, unless indicated otherwise, it may be assumed that description of one such component with respect to one Figure may also be applied to similar components depicted in other Figures, as indicated by the common last two digits of the reference numbers associated with such components.

DETAILED DESCRIPTION

The following description is directed to certain implementations for the purposes of describing the innovative aspects of this disclosure. However, a person having ordinary skill in the art will readily recognize that the teachings herein can be applied in a multitude of different ways. Thus, the teachings are not intended to be limited to the implementations depicted solely in the Figures, but instead have wide applicability as will be readily apparent to one having ordinary skill in the art.

Figure 1:
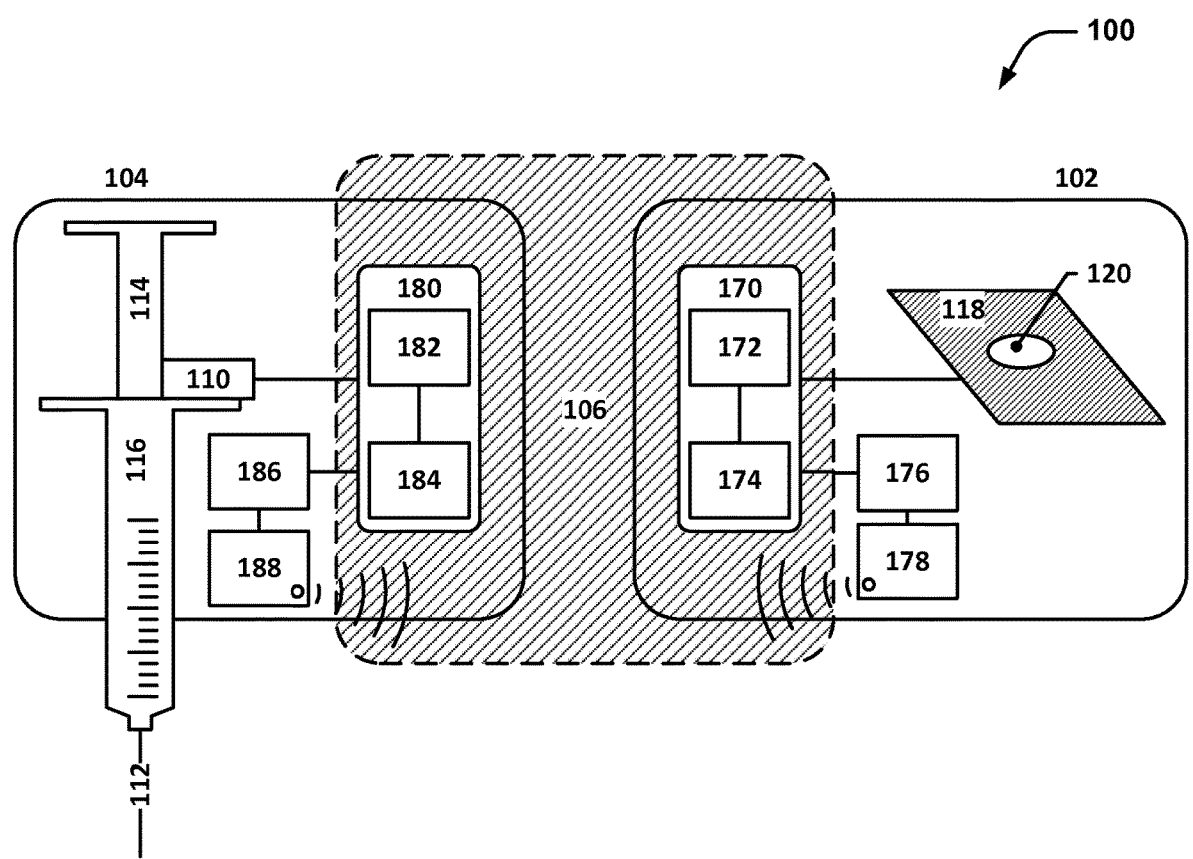
FIG. 1 depicts a system diagram of an example system that includes an adhesive patch and a subcutaneous medication delivery applicator.

FIG. 1 depicts a system diagram of an example system 100 that includes an adhesive patch 102 and a subcutaneous medication delivery applicator (SMDA) 104. The adhesive patch 102 and the SMDA 104 are designed to work together to facilitate proper injectable medication delivery for patients who self-medicate or self-inject.

The adhesive patch 102 may include a flexible substrate 118 with an adhesive backing material on one side and one or more openings 120; the one or more openings 120 indicate post-adhesion, designated injection sites, i.e., target locations that the person administering the injection can aim for when using the SMDA 104 after the adhesive patch 102 has been adhered to the recipient's skin. The adhesive backing may be any adhesive material that may be used to form an adhesive bond between the flexible substrate 118 and a person's skin, and may typically be a non-permanent, hypoallergenic adhesive such as may be used for adhesive bandages or other wearable adhesive systems. Many medications are designed to be injected at particular locations in the human body—for example, insulin is generally injected into the abdomen, outer thigh, upper buttocks, or back of the upper arms. In another example, in-vitro fertilization treatment may require a number of injections administered to the patient's buttocks. Thus, the adhesive patch 102 may serve as a visual indicator of the designated injection sites for a particular medication. In some implementations, the patient may apply the adhesive patch 102 themselves, although in other implementations, the adhesive patch 102 may be applied to the patient by another individual, e.g., the patient's doctor, nurse, or caregiver.

In some implementations, the adhesive patch 102 may include a plurality of openings 120 and each opening 120 may be designated for a particular injection event. For example, the adhesive patch 102 may include seven openings 120, each designating a designated injection site for a different day of the week. By separately indicating the designated injection site for each day of the week, such an example adhesive patch 102 may help the patient avoid administering multiple injections at the same injection site, which can lead to scarring inside the skin.

The adhesive patch 102 may include some form of visual indicator that clearly indicates each opening for the benefit of the person administering the injection. For example, the opening may be outlined with a border or, if the adhesive patch is of color that contrasts with the patient's skin, the color transition across the edge of the opening may provide the visual indicator. This provides a target or "bulls-eye" for the person administering the injection to aim for.

Figure 2:
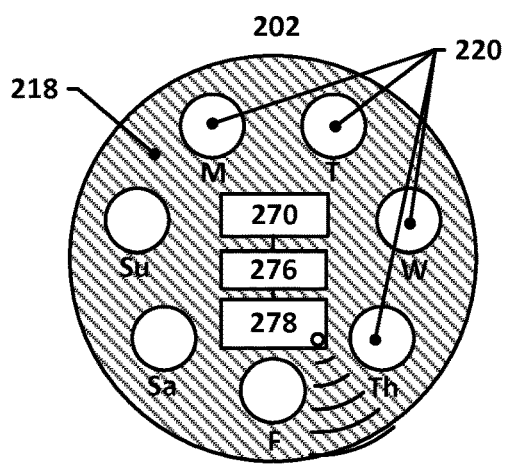
FIG. 2 depicts a diagram of an example adhesive patch that includes a plurality of openings.

In adhesive patches 102 that include multiple openings, each opening may be provided with a different distinguishing characteristic, for example, each opening may be outlined in a different color or marked with a different number or alphanumeric code, symbol, or other visual indicator adjacent to the opening. FIG. 2 depicts a diagram of an example adhesive patch that includes a plurality of openings. As can be seen, an example adhesive patch 202 is depicted in FIG. 2; the example adhesive patch 202 may include a first portion 270 (which includes a processor and memory), a first short-range wireless communications interface 276, and a first antenna 278. The adhesive patch 202 may also include a plurality of openings 220 that are distributed throughout a flexible substrate 218. In this example, the letters M, T, W, Th, F, Sa, Su are used to indicate openings for each of the different days of the week. In other implementations, other types of distinguishing characteristics that may be used may include, for example, different shapes for each opening, such as, for example, circular openings, square openings, triangular openings, star-shaped openings, pentagonal openings, etc. It is to be understood that the distinguishing characteristics listed herein may also be combined to provide additional differences between the openings. For example, the openings may each have a colored border and a different shape, in which case the combination of the two characteristics (shape and border color) may be unique for each opening, but there may, for example, be multiple instances of each individual characteristic. For example, there may be 3 square-shaped openings and 3 circular openings, and each square-shaped opening may be indicated by a different one of a red, green, or blue border, as may each circular opening. Thus, there may be multiple square-shaped openings, and multiple red-bordered openings, but only on red-bordered, square-shaped opening.

In addition to the opening or openings that are included in each adhesive patch 102, the adhesive patch 102 may include a first processor 172, a first memory 174, and a first short-range wireless communications interface 176 connected with a first antenna 178. The first processor 172, the first memory 174, and the first short-range wireless communications interface 176 may be operatively connected to one another such that the first processor 172 may cause the first short-range wireless communications interface 176 to send and receive data via the first antenna 178 and may store and retrieve data from the first memory 174.

Similarly, the SMDA 104 may include a second processor 182, a second memory 184, and a second short-range wireless communications interface 186 connected with a second antenna 188. The second processor 182, the second memory 184, and the second short-range wireless communications interface 186 also may be operatively connected to one another such that the second processor 182 may cause the second short-range wireless communications interface 186 to send and receive data via the second antenna 188 and may store and retrieve data from the second memory 184.

The SMDA 104 shown in FIG. 1 is a standard syringe with a body 116, a plunger 114, and a needle 112. The SMDA 104 may also include a safety interlock 110 that may be operatively connected with the second processor 182. The safety interlock 110 may be configured to prevent the plunger 114 from being moved relative to the body 116 when engaged; the second processor 182 may be configured so that it can disengage the safety interlock 110 to allow the plunger 114 to be moved relative to the body 116, allowing medication contained within the body 116 to be dispensed.

It is to be understood that the SMDA 104 and the safety interlock 110 may take any of a variety of forms. For example, the SMDA 104 may be an autoinjector-type syringe or a jet-injector-type applicator. An autoinjector-type syringe is a hypodermic injector in which the needle is housed within a housing until the autoinjector is used. When the autoinjector housing is pushed against a person's skin, the needle, which is usually spring-loaded, is forced out of the housing and into the person's flesh, after which the medication can be dispensed subcutaneously. If an autoinjector-type SMDA is used, the safety interlock 110 may be configured to prevent the needle from deploying until the safety interlock 110 is disengaged.

A jet-injector-type SMDA or needleless jet-injector-type SMDA is a subcutaneous medication applicator that forms the medication into a narrow, high-pressure jet in order to deliver the medication subcutaneously. The jet of medication forces its way into the skin without the need for a needle. If a jet-injector-type SMDA is used, the safety interlock 110 may be configured to lock the trigger that causes the jet-injector to dispense the medication. As will be evident, the particular mechanism that is used to provide the safety interlock can take any of a variety of forms, all of which are within the scope of this disclosure.

It is also to be understood that the safety interlock, in some implementations, may be reversible. For example, the second processor 182 may be configured to not only disengage the safety interlock 110, but also to re-engage or engage the safety interlock 110. Such reversible safety interlocks 110 may be particularly useful for medication dispensation systems in which a single SMDA 104 is used multiple times, for example, an autoinjector pen or syringe may be reloaded with new medication doses by replacing a spent medication cartridge with a new medication cartridge—in such implementations, it would be beneficial to use a reversible safety interlock so that the autoinjector pen could be reused with the new cartridge and still retain the safety interlock functionality.

The first processor 172, the first memory 174, the second processor 182, and the second memory 184 may, in aggregate, form a distributed control logic 106; the first processor 172 and the second processor 182 may form a first portion 170 of the control logic 106, and the second processor 182 and the second memory 184 may form a second portion 180 of the control logic 106. The control logic 106 may, for example, be configured to provide certain functionality relating to the system. It is also to be understood that the first portion 170 and the second portion 180 may each be equipped with a power supply of some type (not shown), such as a battery, that provides power to the respective electronic systems of each type of device. It is to be further understood that the power supply may be distributed among the various individual components that make up the system, as suggested above, or may be distributed or concentrated in a subset of the components that make up the system. Components that are not equipped with their own power supplies may, instead, have subsystems that may obtain power from other components that do. For example, one component with a power supply may have an inductive charging coil that may be used to provide power to another component in the system that does not have its own power supply, but does have an inductive loop for receiving power from the inductive charging coil. In other implementations, the power may be transferred from one component to another within the system using a cable that may be used to temporarily link the component with a power supply to the component(s) that does not. In some implementations, one or more components of the system may include other power-generation features that may be used in place of a power supply. For example, an adhesive patch or SMDA may include one or more photovoltaic cells that provide electrical energy to the adhesive patch when exposed to light. It is to be understood that this concept extends to SMDAs that contain power supplies that may be used to provide power to adhesive patches that do not have their own dedicated power supplies, as well as adhesive patches that contain power supplies that may be used to provide power to SMDAs that do not have their own dedicated power supplies, as well as other potential implementations of such systems.

Generally speaking, one of the core functionalities provided by the control logic is to control the disengagement of the safety interlock 110 only under certain circumstances, namely in situations in which the SMDA 104 is in close proximity to the adhesive patch 102 and the SMDA 104 and the adhesive patch 102 can be verified as being pre-associated with one another. In this context, the adhesive patch 102 serves as a proxy for the patient (since it is presumably adhered to the patient, this is a reasonable assumption) and the SMDA 104 serves as a proxy for the medication—if the adhesive patch 102 and the SMDA 104 can be verified as being associated with one another, then this association may act as a proxy for an association between the patient and the medication.

In some implementations, such an association may be pre-established at a manufacturer of the system. For example, a manufacturer provisioning an injection kit may include one or more SMDAs 104 and one or more adhesive patches 102 in the kit, and each SMDA 104 and adhesive patch 102 in the kit may be provided with some form of identifier that uniquely associates them with one another. For example, each SMDA 104 and/or adhesive patch 102 may be provided with the same serial number that is unique to the kit, and the control logic may later determine that an SMDA 104 and an adhesive patch 102 are associated when both the SMDA 104 and the adhesive patch 102 provide matching serial numbers. In another example, each SMDA 104 and adhesive patch 102 may be provided with a unique serial number that uniquely identifies each such device—however, each SMDA 104 and/or each adhesive patch 102 may also store the unique serial numbers of the other components of the kit in memory, for example, each SMDA 104 may store the serial number of each adhesive patch 102 of the kit in the second memory 184, allowing the SMDA 104 to determine if a particular adhesive patch 102 with which it is in communication has a unique serial number that matches one of the pre-stored serial numbers, which would thus establish a pre-association between the SMDA 104 and the adhesive patch 102. It is to be understood that SMDAs from multiple, different manufacturers and/or multiple SMDAs, each containing different medications, may be used with a single adhesive patch (or series of adhesive patches). In such implementations, the control logic may track each SMDA or medication separately, and, each time a particular SMDA or medication injection is attempted, may check to see if that particular SMDA or medication is pre-associated with the adhesive patch currently being worn. In practice, when an SMDA 104 is to be used, the person administering the medication in the SMDA 104 may first bring the SMDA 104 into close proximity with the adhesive patch 102 in order to establish a wireless communications connection between the two devices via the second short-range wireless communications interface 186 and the first short-range wireless communications interface 176, respectively. Once the wireless communications connection is established, information, such as unique identifiers for one or both of the SMDA 104 and the adhesive patch 102, may be sent between the SMDA 104 and the adhesive patch 102 that allows the control logic 106 to determine if the SMDA 104 and the adhesive patch 102 are associated with one another.

Figure 3:
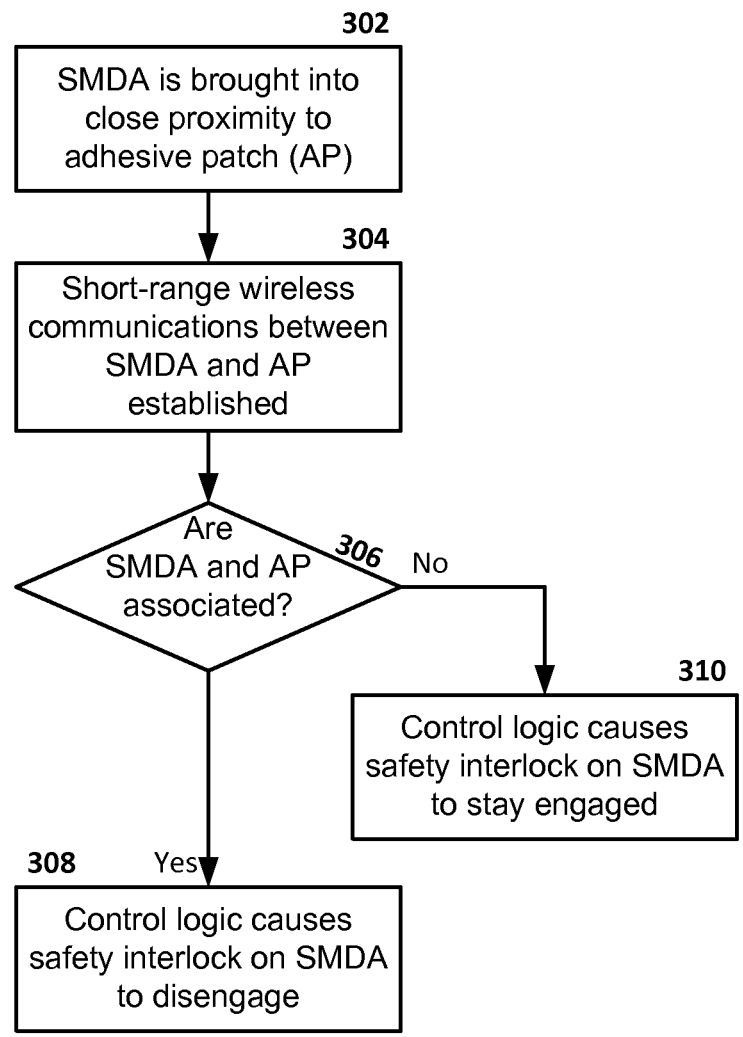
FIG. 3 depicts a flow diagram of one example technique that may be used to disengage a safety interlock of a subcutaneous medication delivery applicator (SMDA).

FIG. 3 depicts a flow diagram of one example technique that may be used to disengage a safety interlock of an SMDA. The technique may begin in block 302, in which an adhesive patch and an SMDA are brought into close enough proximity to one another that a communications connection can be established via the first and second short-range wireless communications interfaces in the adhesive patch and SMDA, respectively, as occurs in block 304. In block 306, control logic, as described above, may evaluate information from the adhesive patch and the SMDA to determine if there is an association between the two components. If so, then the technique proceeds to block 308, where the control logic causes a safety interlock of the SMDA to become disengaged. If not, then the technique proceeds to block 310, in which the control logic causes the safety interlock of the SMDA to remain engaged in order to prevent unauthorized use.

The first short-range wireless communications interface 176 and/or the second short-range wireless communications interface 186 may have a range on the order of several inches to several feet, for example, 3-4 feet, which may ensure that the communications link between the SMDA 104 and the adhesive patch 102 only exists when the SMDA 104 and the adhesive patch 102 are presumably within the direct presence of each other. In other words, they are close enough to one another that it is unlikely that the person wearing the adhesive patch 102 is unaware that the SMDA 104 is about to be used. Technologies that may provide such a suitably short-range communications connection include, but are not limited to, radio-frequency identification (RFID) and near-field communications (NFC) technologies.

For example, the first short-range wireless communications interface 176 may include an NFC device that may be interrogated by an NFC reader in the second short-range wireless communications interface 186 when within range (typical NFC devices typically have ranges on the order of one to two inches, so the SMDA 104 may need to be brought directly adjacent to the adhesive patch 102; using RFID technology may provide slightly greater range). If the adhesive patch 102 provides information to the SMDA 104 in response to this interrogation that allows the control logic 106 to verify that the adhesive patch 102 and the SMDA 104 are associated, the control logic 106 may then cause the safety interlock 110 to be disengaged, allowing the SMDA 104 to be used to administer the medication.

This authentication process may be automatic. For example, the SMDA 104 may periodically scan for a nearby first short-range wireless communications interface 176 and then initiate the authentication process and potential safety interlock 110 disengagement upon detection of a nearby first short-range wireless communications interface 176. In other implementations, this process may involve one or more additional steps. For example, one or both of the SMDA 104 and the adhesive patch 102 may include some form of activation control that may be used to place the SMDA 104 and/or the adhesive patch 102 into a state in which communication with the other device is attempted, or into a state in which authorization for medication injection is to be attempted. Such a feature may allow for reduced power consumption, as the SMDA 104 and the adhesive patch 102 may be kept in an off or low-power state until activated for an attempted injection. This feature may also be of use in implementations in which there are multiple SMDAs 104 and/or multiple adhesive patches 102 in a kit. In such implementations, it may be desirable to only enable one SMDA 104 and one adhesive patch 102 from the kit at a time to avoid, for example, disengaging the safety interlock 110 of more than one SMDA 104 at a time or to avoid having adhesive patches 102 that are not applied to the patient but that may be stored near the SMDAs 104 (such as may be the case if the adhesive patches 102 and the SMDAs 104 in the kit are supplied in a common pouch or case) trigger disengagement of the safety interlocks 110 of the SMDAs 104 stored nearby.

In some implementations, the adhesive patch 102 may be equipped with technology that causes the adhesive patch 102 to remain in an inactive or sleep state until it is applied to the patient. For example, the adhesive patch 102 may include two spaced-apart electrodes that produce an electrical signal when brought into contact with human flesh, such as may occur when the adhesive patch 102 is applied to the patient and the patient's skin provides a conductive path between the two electrodes. The adhesive patch 102 may remain in a low-power state, intermittently sampling the electrodes, until the electrodes provide the electrical signal that indicates that the adhesive patch 102 has been applied to the patient's skin. Upon receiving such a signal, the first processor 172 may transition the adhesive patch 102 to a higher power state, including activating the first short-range wireless communications interface 176 so that it can be used to communicate with the second short-range wireless communications interface 186. Thus, the adhesive patch 102 in such cases may only be "active" when adhered to a patient's skin. In other implementations, other skin-detection technologies may be used to detect when the adhesive patch 102 is applied to a person's skin. For example, in some implementations, a capacitively-based skin detection sensor may be used to determine if the adhesive patch 102 has been applied to a person's skin by measuring a change in capacitance based on the proximity of human flesh.

In some additional or alternative implementations of the adhesive patch 102, the adhesive patch 102 may also be configured to disable itself upon removal from the patient's skin. For example, the dual-electrode implementation discussed above also may provide an electrical signal when the adhesive patch 102 is removed from the patient's skin and the electrical resistance between the electrodes changes. The first processor 172 may be configured to cause the adhesive patch 102 to render itself inoperative in response to receiving such an electrical signal. For example, the first processor 172 may cause the adhesive patch 102 to short-circuit various critical components or to disconnect the power supply of the adhesive patch 102.

The control logic 106 may, in addition to verification of an association between the SMDA 104 and the adhesive patch 102, provide additional functionality. For example, the control logic 106 also may track each time that the SMDA 104 or SMDAs 104 are used to dispense medication, and may store information regarding such events in memory, for example, in first memory 174, second memory 184, or another memory. A variety of different techniques may be used by the control logic 106 to determine if an SMDA 104 has been used to dispense medication. For example, the control logic 106 may be configured to track each time that it causes the safety interlock 110 of an SMDA 104 to disengage and to treat each such safety interlock 110 disengagement as equivalent to the dispensation of the medication, on the assumption that each time the safety interlock 110 is disengaged, the medication is dispensed.

In other implementations, the control logic 106 may identify medication dispensation events with greater certainty or based on other or additional factors. For example, the SMDA 104 may include a sensor that may indicate when, for example, a plunger of the SMDA 104 has been moved in a manner that would cause medication to be dispensed. In some such implementations, the sensor also may indicate the amount of such movement, allowing for an estimate of the amount of such medication that is dispensed to be calculated by the control logic 106. In some further or alternative such implementations, the control logic 106 may also obtain data from sensors in the adhesive patch 102, to provide further certainty as to whether or not medication was actually dispensed from the SMDA 104 at a particular time.

For example, in some implementations of the adhesive patch 102, the adhesive patch 102 also may include a sensor that is configured to detect when the needle of an SMDA 104 (for SMDAs 104 that have needles) has been inserted into the patient's skin. One such type of sensor is an inductive loop that encircles the opening(s) 120. Since needles are metallic, their proximity to such an inductive loop housed within the adhesive patch 102 may cause a magnetic field induced by the inductive loop to fluctuate, which may be detected by circuitry connected with the inductive loop. Such a sensor may provide an indication that the SMDA 102's needle 112 has been moved proximate to the designated injection site.

Figure 4:
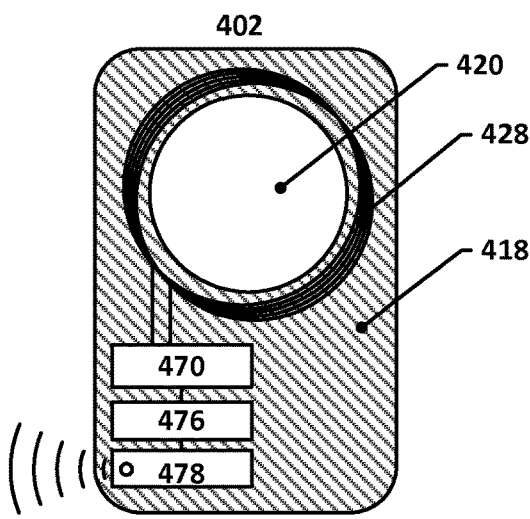
FIG. 4 depicts an example adhesive patch with an inductive loop proximity sensor.

FIG. 4 depicts an example adhesive patch with an inductive loop proximity sensor. As can be seen, FIG. 4 depicts an adhesive patch 402 that includes a first portion 470 (which may include a first processor and a first memory) that is operatively connected with a first short-range wireless communications interface 476 and a first antenna 478. The first portion 470 also may be connected with an inductive loop sensor 428 that encircles an opening 420 in a flexible substrate 418 of the adhesive patch 402. This inductive loop sensor 428 may, as discussed above, be used by the first portion 470 to determine if a needle is in close proximity, as would occur during an injection event.

Another type of sensor that may be used is a bioimpedance sensor that measures bioimpedance through the skin across each opening 120. Such a sensor, for example, may include two electrodes that may conduct a microcurrent through the skin within the opening 120. When the needle 112 is inserted into the skin within the opening 120, the metal of the needle may cause the local bioimpedance of the skin to change, which may be measured by the bioimpedance sensor and registered as a needle insertion event.

In some implementations, the medication that is being delivered via the SMDA 104 may cause physiological changes in the patient in the immediate area of the injection that may be detectable by a sensor that may be included in the adhesive patch 102. For example, the medication may alter the pH of the person's skin in the region of the injection, which may be detectable as a change in bioimpedance in that region. If this is the case, then a bioimpedance sensor, for example, a dual-electrode sensor such as is described above, may be able to detect such changes and provide an indication as to when the medication was actually administered—this may provide even greater assurance that a particular medication administration even has occurred. It is to be understood that while the previous example focused on a dual-electrode bioimpedance sensor, other types of sensors that may be used may include sensors that have more than two electrodes, e.g., three, four, etc. electrodes. In some implementations, non-impedance sensors may be used to measure a physiological change, including, for example, photoplethysmographic or other optically-based sensors.

Figure 5:
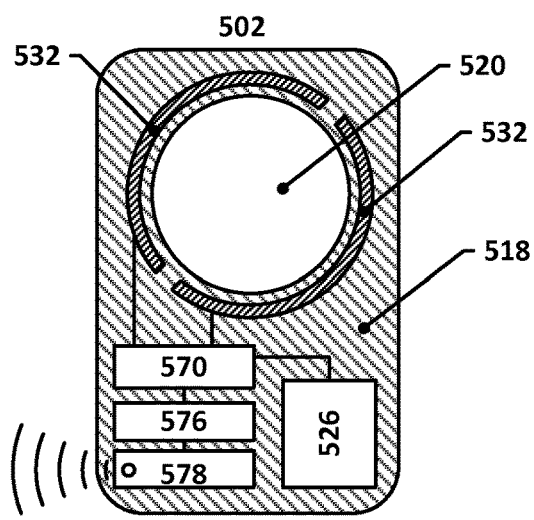
FIG. 5 is a diagram of an example adhesive patch that includes electrodes for detecting bioimpedance changes in a person's skin.

FIG. 5 is a diagram of an example adhesive patch that includes electrodes for detecting bioimpedance changes in a person's skin. As can be seen, FIG. 5 depicts an adhesive patch 502 that includes a first portion 570 (which may include a first processor and a first memory) that is operatively connected with a first short-range wireless communications interface 576 and a first antenna 578. The first portion 570 also may be connected with two (or more) electrodes 532 that are positioned proximate to an opening 520 in a flexible substrate 518 of the adhesive patch 502. These electrodes 532 may, as discussed above, be used by the first portion 570 to determine if there has been a change in local bioimpedance within the skin of a wearer of the adhesive patch 502, as would occur during an injection event. As can be seen, the electrodes 532 are electrically isolated from one another within the adhesive patch 502 so as to route electrical current between the electrodes 532 through the wearer's skin.

The control logic 106 may be configured to track medication application events, as discussed above, and to store a log of each medication application event in memory for later reference, or to transmit information regarding each medication application event to another device, for example, to a remote server. In some implementations of the system 100, each time an attempt is made to use an SMDA 104, the control logic 106, in addition to verifying that the SMDA 104 is associated with the adhesive patch 102, also may determine the most recent time that a medication application event occurred and, if such an occurrence was within a certain threshold of time, such as a minimum amount of time that must elapse between doses of the medication per the prescribing doctor's instructions or the medication manufacturer's instructions, the control logic 106 may leave the safety interlock 110 engaged to prevent premature re-dosing or overdosing. In some such implementations, the SMDA 104 or the adhesive patch 102 also may be equipped with an alert device, such as some form of visual, auditory, or haptic indicator, that the control logic 106 may cause to provide an indication to the patient that medication dispensation is not authorized due to the fact that sufficient time has not elapsed since the most recent dose was administered. In implementations where multiple SMDAs are used, such as SMDAs containing different medications, the control logic may monitor a corresponding number of dosage thresholds, and track when each SMDA or medication was injected. When a re-injection of a previously-injected medication is attempted, the elapsed time since the most recent previous injection of that medication and/or SMDA may be evaluated to see if it exceeds an associated threshold amount of time between doses for that medication and/or SMDA. The threshold amount of time between doses for each medication may differ from medication to medication or SMDA to SMDA. If the time since the most recent previous injection of a medication does not exceed the threshold amount of time between doses for that medication, the control logic may, as discussed above, cause the safety interlock for that SMDA to remain engaged—even though the control logic may also, at the same time, allow the safety interlock of another SMDA to disengage if there has been sufficient time since the most recent previous injection of the medication associated with that other SMDA according to a threshold amount of time between doses for that medication.

Figure 6:
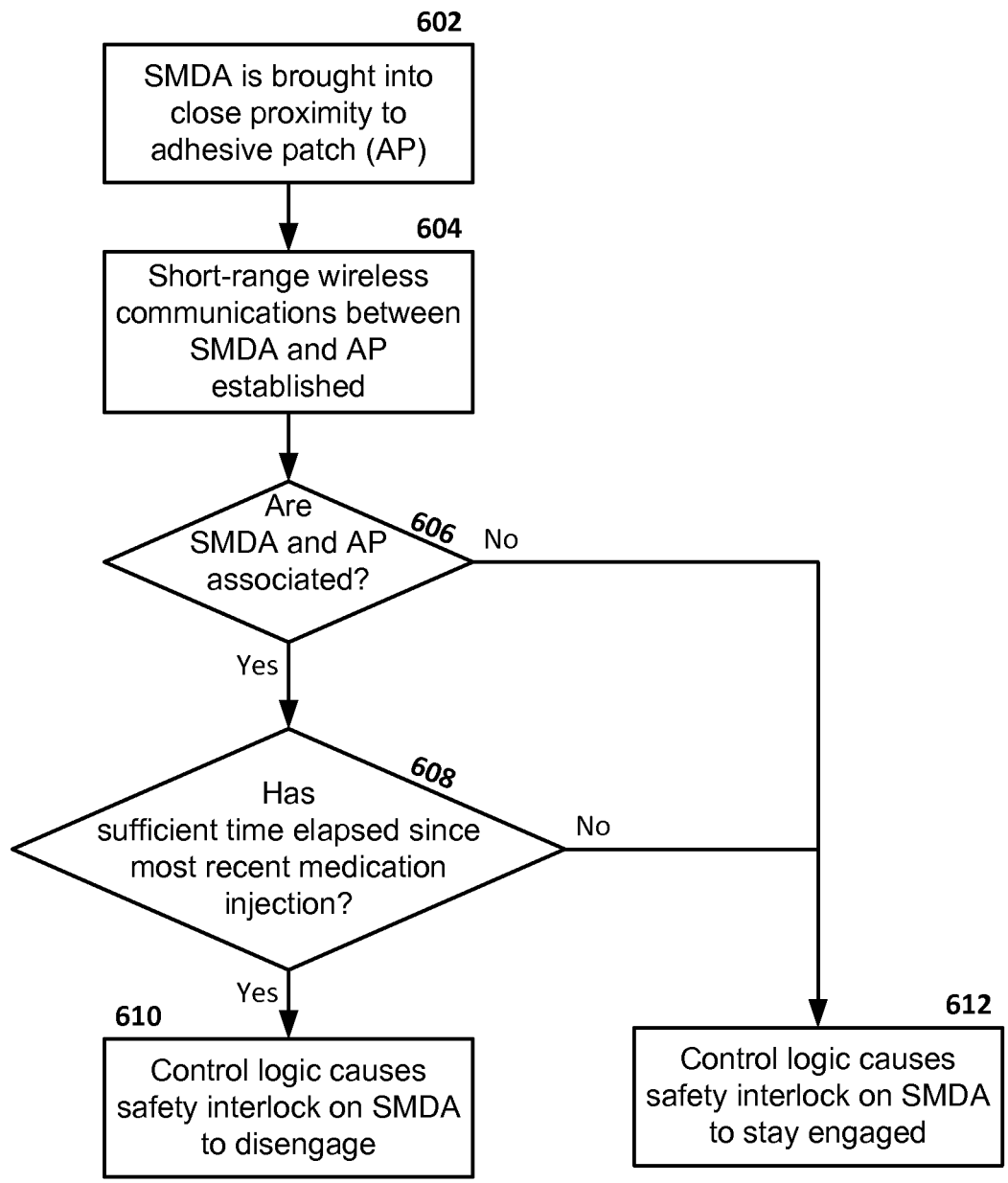
FIG. 6 depicts a flow diagram for one example technique of determining whether or not a safety interlock should be disengaged based on establishing an association between an SMDA and an adhesive patch in addition to accounting for the amount of time since a particular medication has been administered.

FIG. 6 depicts a flow diagram for one example technique of determining whether or not a safety interlock should be disengaged based on establishing an association between an SMDA and an adhesive patch in addition to accounting for the amount of time since a particular medication has been administered. The technique of FIG. 6 begins in block 602, in which an SMDA is brought into close enough proximity to an adhesive patch that a short range wireless communications connection between the adhesive patch and the SMDA may be established via the short-range wireless communications interfaces of the two devices in block 604.

After such a communications connection is established, the technique may proceed to block 606, in which the control logic for the system may determine if the SMDA and the adhesive patch are associated with one another. If not, then the technique may proceed to block 612, where the control logic may prevent disengagement of a safety interlock of the SMDA. However, if the control logic determines that there is an association between the SMDA and the adhesive patch in block 606, then the control logic may proceed to block 608, in which the control logic may determine how long it has been since the most recent application or injection of medication has occurred. If insufficient time has elapsed since the most recent application or injection of medication has occurred, then the technique may proceed to block 612 and the safety interlock may remain engaged. However, if sufficient time has elapsed since the most recent injection of medication, then the control logic may proceed to block 610 and disengage the safety interlock to allow for a further injection to occur.

In some such implementations, the control logic 106 may, in addition to tracking when medication administration events have occurred, track when medication administration events should occur based on various factors, including, for example, the time at which the most recent administration of medication occurred or a specific time of day at which the medication should be administered. For example, when performing egg retrieval from a woman in the context of infertility treatment, it is common for a series of daily injections to be performed in order to stimulate egg follicle production in the ovaries, followed by a "trigger shot" of human chorionic gonadotropin (hCG) that must typically be administered 36 hours prior to the scheduled egg retrieval procedure in order to cause ovulation to occur at approximately the same time as when the egg retrieval is attempted; if this shot is administered more than 1 hour off schedule, then ovulation may occur too late or too early, and the egg retrieval procedure may be unsuccessful. An adhesive patch 102 may be equipped with functionality that may assist with ensuring that such medication injection occurs at the desired time by alerting the patient by way of an alert mechanism, such as a visual, auditory, or haptic device.

Figure 7:
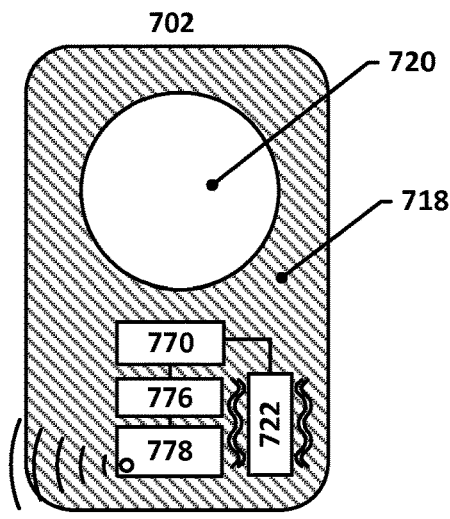
FIG. 7 depicts an example adhesive patch that includes a feedback device to provide cues to the patient that it is time to inject a medication.

FIG. 7 depicts an example adhesive patch that includes a feedback device to provide cues to the patient that it is time to inject a medication. As can be seen in FIG. 7, the adhesive patch 702 includes a flexible substrate 718 with an opening 720, as well as a first portion 770 (which may include a first processor and a first memory) that is operatively connected with a first short-range wireless communications interface 776 and a first antenna 778. The first portion 770 also may be connected with a haptic feedback device 722 that may be activated by the first portion 770 when the control logic of which the first portion 770 is part determines that it is time to inject a medication. The control logic may be configured to activate the haptic feedback device 722 on a particular date and at a particular time, for example, based on a scheduled egg retrieval procedure in the context of infertility treatments, or based on the elapsed time since a previous application of medication. It is to be understood that in addition to, or in the alternative to, the haptic feedback device 722, other types of feedback devices may be used, such as audio speakers or even visual indicators (although the latter likely has a reduced efficacy since many adhesive patches 102 will be worn underneath the patient's clothes, making it difficult or impossible to notice a visual indicator. In some implementations where the control logic may be configured to keep the safety interlock of the SMDA engaged if a repeat administration of the medication is attempted before a minimum allowable amount of time elapses since the most recent medication application, the control logic may be configured to activate the haptic feedback device 722 after the minimum allowable amount of time elapses in order to alert the patient that they may now attempt to inject the medication again. In some implementations, such as the implementation discussed below with respect to FIG. 14, the control logic may also include a portion included in a mobile electronic device, such as a smartphone. In such cases, the control logic may also or alternatively be configured to cause the mobile electronic device to provide a notification that a medication application should be performed, such as by causing the mobile communications device to provide an audible alert or to vibrate in association with an on-screen message to the patient that the medication application should be performed.

Figure 8:
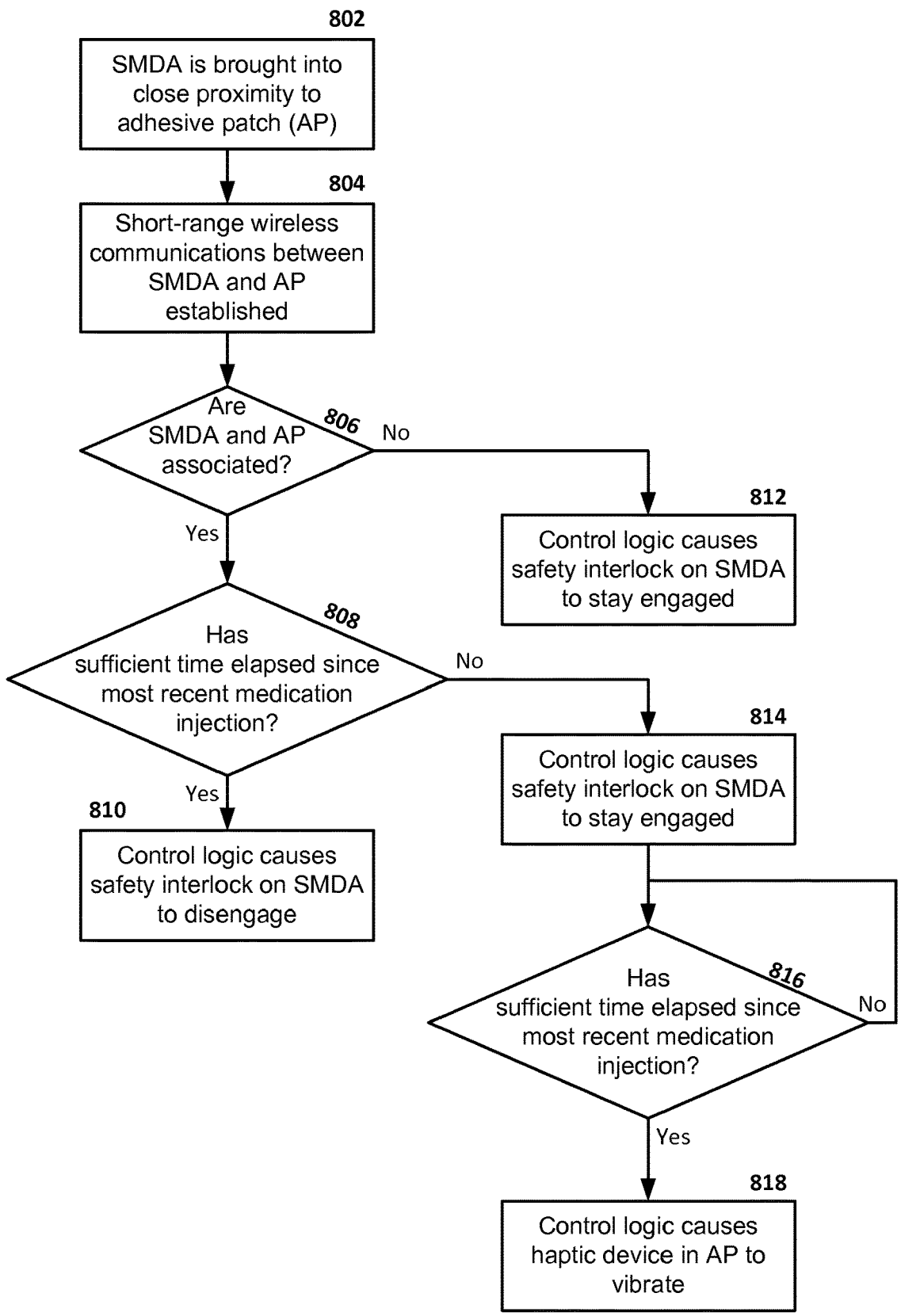
FIG. 8 depicts a flow diagram for one example technique of determining whether or not a safety interlock should be disengaged based on establishing an association between an SMDA and an adhesive patch in addition to accounting for the amount of time since a particular medication has been administered; the technique also includes providing an indication as to when a sufficient amount of time has elapsed.

FIG. 8 depicts a flow diagram for one example technique of determining whether or not a safety interlock should be disengaged based on establishing an association between an SMDA and an adhesive patch in addition to accounting for the amount of time since a particular medication has been administered; the technique also includes providing an indication as to when a sufficient amount of time has elapsed. The technique of FIG. 8 begins in block 802, in which an SMDA is brought into close enough proximity to an adhesive patch that a short range wireless communications connection between the adhesive patch and the SMDA may be established via the short-range wireless communications interfaces of the two devices in block 804. After such a communications connection is established, the technique may proceed to block 806, in which the control logic for the system may determine if the SMDA and the adhesive patch are associated with one another. If not, then the technique may proceed to block 812, where the control logic may prevent disengagement of a safety interlock of the SMDA. However, if the control logic determines that there is an association between the SMDA and the adhesive patch in block 806, then the control logic may proceed to block 808, in which the control logic may determine how long it has been since the most recent application or injection of medication has occurred. If sufficient time has elapsed since the most recent injection of medication, then the control logic may proceed to block 810 and disengage the safety interlock to allow for a further injection to occur. If insufficient time has elapsed since the most recent application or injection of medication has occurred, then the technique may proceed to block 814 and the safety interlock may remain engaged. The technique may then proceed to block 816, in which the control logic may determine if sufficient time has elapsed since the most recent medication injection occurred. If so, then the control logic may cause a haptic device in the adhesive patch to vibrate in block 818 to indicate to the patient that sufficient time has elapsed—when the patient then attempts to use the SMDA with the adhesive patch, then the control logic will disengage the safety interlock (for example, the technique may start again at block 802 and proceed to block 810). If not, then the technique may return again to block 816 until sufficient time has elapsed.

Figure 9:
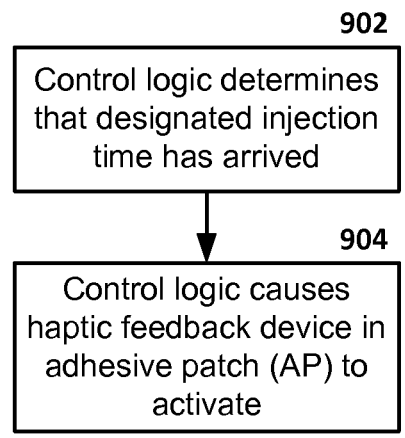
FIG. 9 depicts a flow diagram of an example technique for alerting a patient to a scheduled medication injection.

FIG. 9 depicts a flow diagram of an example technique for alerting a patient to a scheduled medication injection. In block 902 of the technique, the control logic may determine that the time of a scheduled injection, such as an hCG trigger shot, has arrived. In block 904, the control logic may cause a haptic feedback device in the adhesive patch to activate to alert the patient that it is time to inject the medication.

In some implementations, the past history of medication application events may be stored on one or both of the SMDA 104 and the adhesive patch 102, for example, in one or both of the second memory 184 and the first memory 174, respectively. If multiple SMDAs and/or adhesive patches are used within a system, then data regarding past medication application events may, for example, be stored on the adhesive patch and then replicated to each SMDA that is used with that adhesive patch so that each SMDA has "knowledge" of events involving previously-used SMDAs. This may allow the second portion, including the second processor and second memory, of an SMDA to evaluate whether or not sufficient time has elapsed since the most recent application of medication using a different SMDA—the current SMDA may obtain a "memory" of such a prior medication delivery from the adhesive patch, which was involved in the medication delivery from the previous SMDA.

Figure 10:
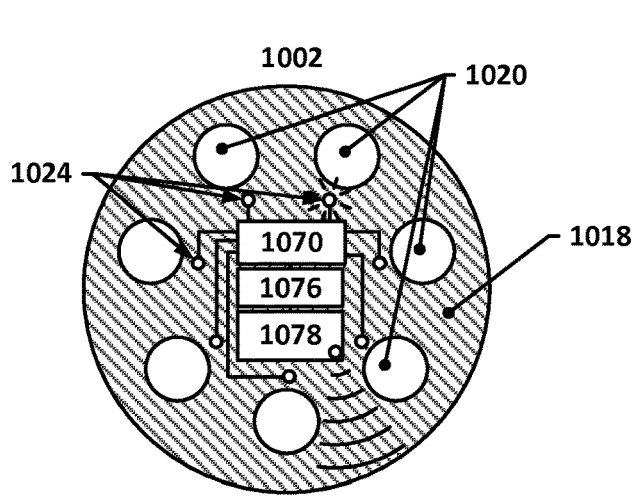
FIG. 10 depicts a diagram of an example adhesive patch that includes a plurality of openings in conjunction with a plurality of switchable visual indicators.

In some implementations, the adhesive patch also may include a plurality of openings as well as a plurality of switchable visual indicators, such as lights or light-emitting diodes (LEDs). FIG. 10 depicts a diagram of an example adhesive patch that includes a plurality of openings in conjunction with a plurality of switchable visual indicators. As can be seen in FIG. 10, an adhesive patch 1002 is depicted that includes a first portion 1070 (which may include a first processor and a first memory) that is operatively connected with a first short-range wireless communications interface 1076 which is, in turn, connected with a first antenna 1078. The adhesive patch 1002 also includes a flexible substrate 1018 with a plurality of openings 1020, as well as a plurality of switchable visual indicators 1024 that are each positioned adjacent to one of the openings 1020. Each switchable visual indicator 1024 may be controllable by the first portion 1070 such that the first portion 1070 may cause each switchable visual indicator to change states. The control logic of which the first portion 10DD70 forms a part may be configured to cause the switchable visual indicators to change state such that a particular designated injection site is indicated. For example, the switchable visual indicator 1024 for a particular designated injection site may be caused by the control logic to blink or illuminate (the other switchable visual indicators 1024 may be caused to enter an off or unilluminated state). In such implementations, the control logic may be configured to cause the switchable visual indicators 1024 to indicate a different opening 1020 each time medication is to be administered using an SMDA.

Figure 11:
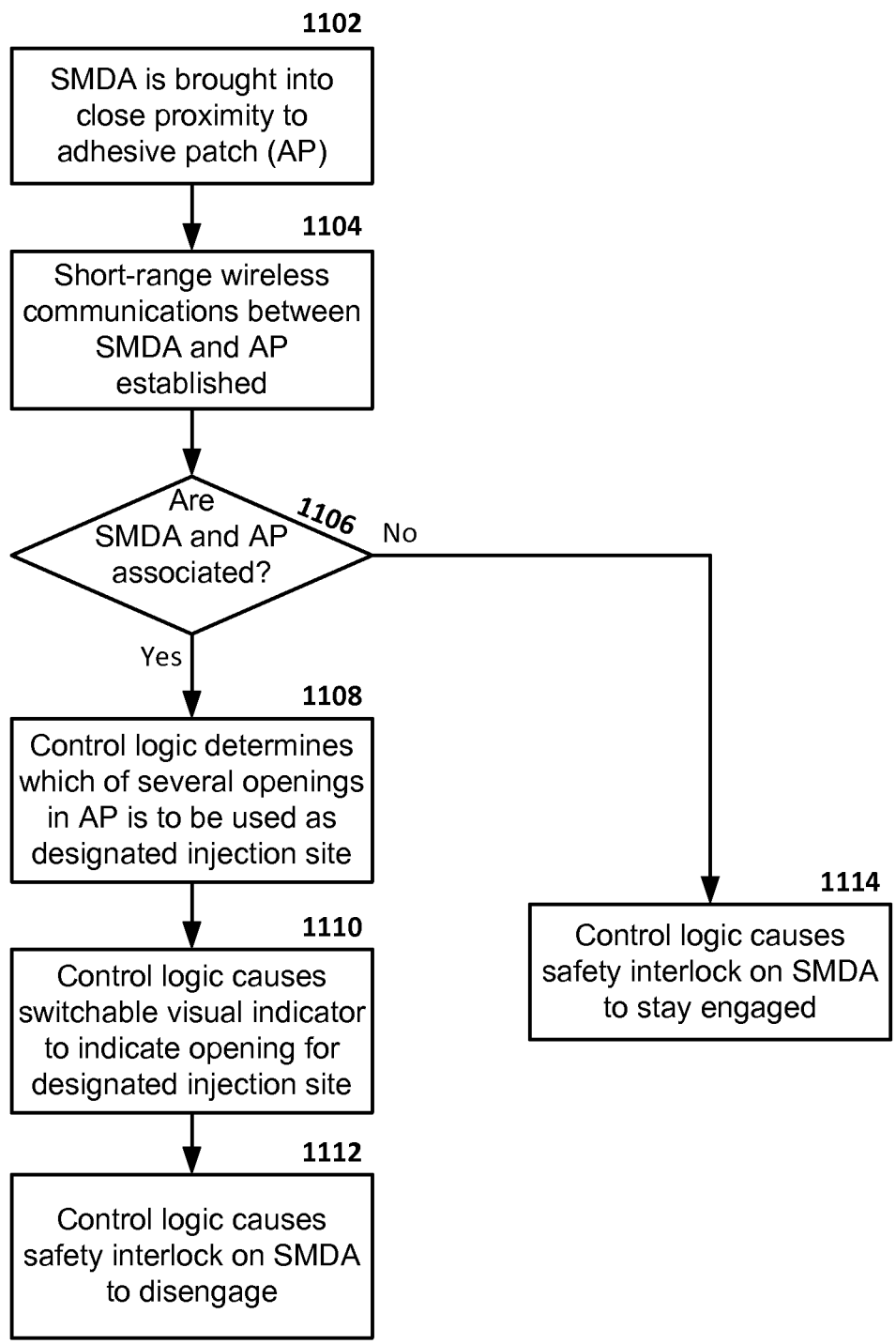
FIG. 11 depicts a flow diagram for an example technique for indicating a particular designated injection site in an adhesive patch.

FIG. 11 depicts a flow diagram for an example technique for indicating a particular designated injection site in an adhesive patch. The technique may begin in block 1102, in which an SMDA is brought into close enough proximity to an adhesive patch that a short range wireless communications connection between the adhesive patch and the SMDA may be established via the short-range wireless communications interfaces of the two devices in block 1104. After such a communications connection is established, the technique may proceed to block 1106, in which the control logic for the system may determine if the SMDA and the adhesive patch are associated with one another. If not, then the technique may proceed to block 1114, where the control logic may prevent disengagement of a safety interlock of the SMDA. However, if the control logic determines that there is an association between the SMDA and the adhesive patch in block 1106, then the control logic may proceed to block 1108, in which the control logic may determine which of several designated injection sites is to be used for the current injection. In block 1110 the control logic may cause a switchable visual indicator adjacent to the selected designated injection site to illuminate or otherwise indicate the selected designated injection site. In block 1112, the control logic may cause the safety interlock to disengage.

Figure 12:
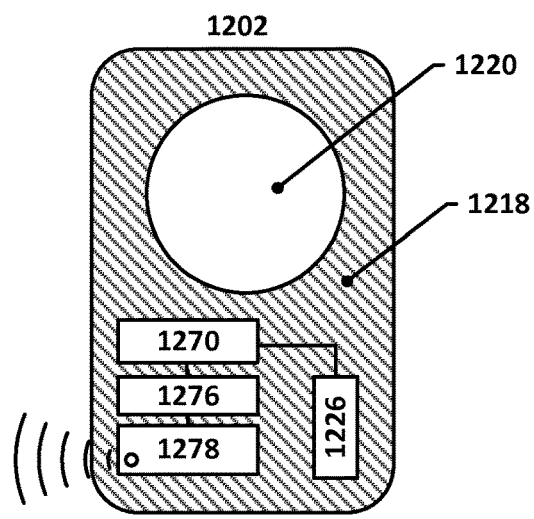
FIG. 12 depicts an example adhesive patch that includes a transdermal medication delivery device.

In some other or additional implementations of the adhesive patch 102, the adhesive patch 102 may be equipped with a medication-dispensing mechanism that may be configured to administer a medication transdermally. FIG. 12 depicts an example adhesive patch with a flexible substrate 1218 and an opening 1220; the adhesive patch 1202 also includes a transdermal medication delivery device. As can be seen in FIG. 12, the adhesive patch 1202 includes a first portion 1270 (which may include a first processor and a first memory) that is operatively connected with a first short-range wireless communications interface 1276 and a first antenna 1278. The first portion 1270 also may be connected with a transdermal medication dispenser 1226, and be operable to control the rate at which the transdermal medication dispenser 1226 administers medication. The transdermal medication dispenser 1226 may utilize, for example, iontophoresis, in which an electrical field may be used to drive an ionic medication through a person's skin—such medication delivery is frequently referred to as "electromotive drug administration" and may provide a mechanism for continuous or long-term medication delivery to a patient. In some circumstances, it may be desirable to adjust the rate of transdermal medication delivery in response to a medication injection being performed. For example, the transdermal medication may interfere with the medication that is to be injected, or there may be concerns that the two medications may produce an undesirable side effect when mixed. In such situations, the control logic of which the first portion 1270 is part may cause the transdermal medication dispenser to adjust the rate at which the transdermal medication is delivered—for example, the transdermal delivery rate may be decreased or turned off entirely. In some implementations, non-iontophoretic transdermal delivery technology may be incorporated into the adhesive patch and may be controlled in order to modulate the rate of medication delivery via the adhesive patch. For example, a transdermal medication dispenser may deliver medication through a membrane that is supplied the medication from a reservoir via a valve or one or more other fluid control devices. The rate at which the medication is dispensed may, for example, be modified by adjusting the state of the valve or other fluid control device.

In some implementations, a transdermal delivery system may be combined with a physiological sensor to provide a more intelligent delivery of medication. For example, in the adhesive patch 502, a transdermal medication delivery device 526 may be communicatively connected with the first portion 570, and the first portion 570 may cause the transdermal medication delivery device 526 to adjust the rate of medication delivery based on changes in bioimpedance measured by the electrodes 532. In other implementations, feedback from other or additional sensors connected with or contained within the adhesive patch 502 that measure physiological parameters relating to the patient may be used by the first portion 570 in order to adjust the medication dispensation rate for the transdermal medication delivery device 526.

While the above examples have focused on systems in which the adhesive patch 102 and the SMDA 104 operate in conjunction with one another to provide the control logic 106 in the relative absence of other components, the systems discussed herein may distribute the control logic 106 across more than just these two components. One or more additional components or devices providing some form of processing capabilities may also be included in the system to provide elements of the control logic 106; an example of one such implementation is discussed in greater detail below.

Figure 14:
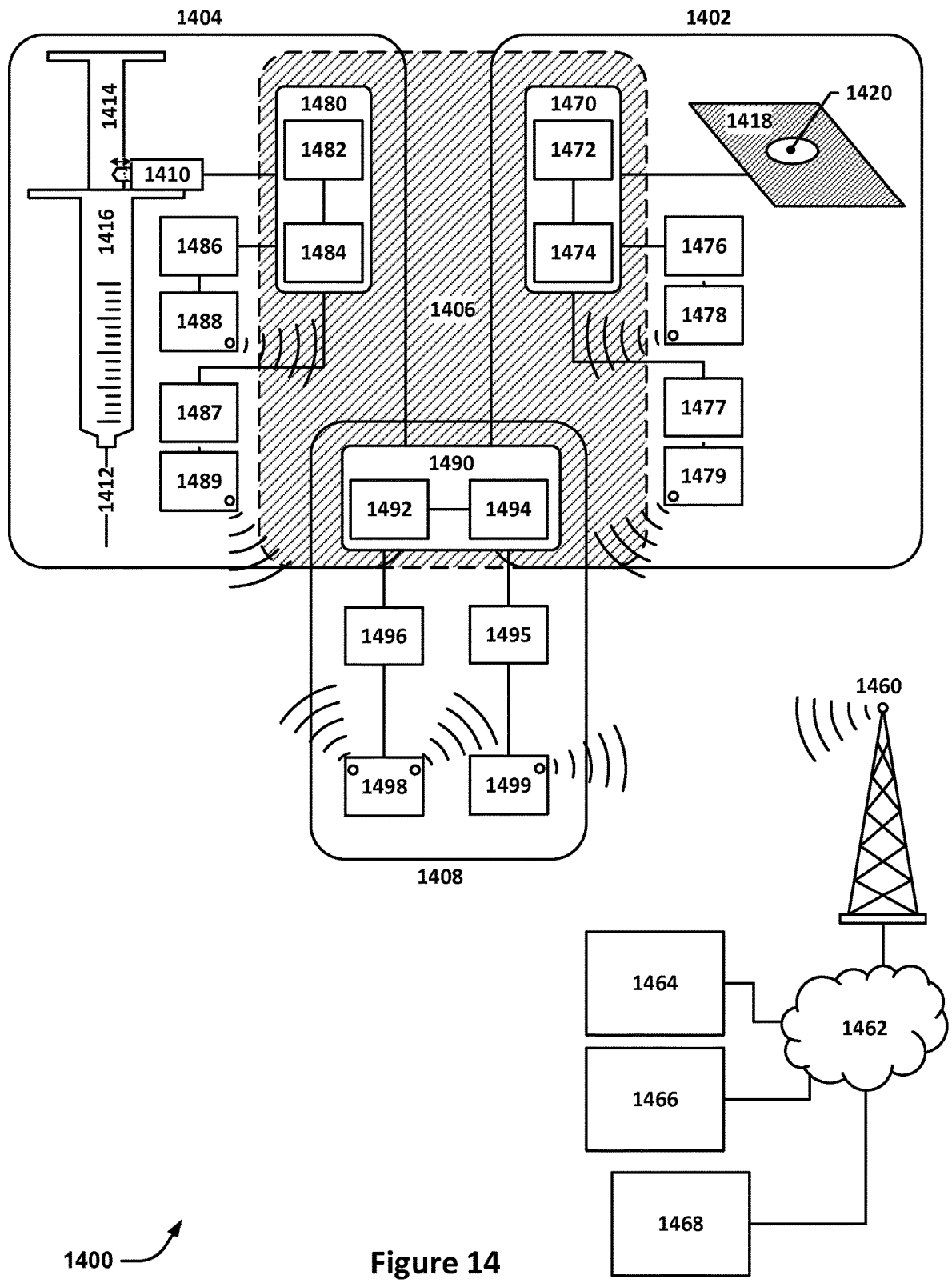
FIG. 14 depicts a system diagram of an example system that includes an adhesive patch, an SMDA, and a mobile communications device.

FIG. 14 depicts a system diagram of an example system 1400 that includes an adhesive patch 1402, an SMDA 1404, and a mobile communications device 1408. In many respects, the system 1400 is similar to the system 100, and similar components in both systems have been indicated using numeric callouts having the same last two digits. For the sake of brevity, these common components are not re-described below, and it is to be understood that the prior description of these components with respect to FIG. 1 is also applicable to the equivalent components in FIG. 14.

The mobile communications device 1408 may, for example, be a smartphone, tablet computing device, laptop, watch or other wearable mobile computing device, or other computing device that includes a third processor 1492 and a third memory 1494 that may form a third portion 1490 of the control logic 1406. In the implementation shown, the adhesive patch 1402, the SMDA 1404, and the mobile communications device 1408 are all equipped with mid-range wireless communications interfaces, such as a first mid-range wireless communications interface 1477, a second mid-range wireless communications interface 1487, and third mid-range wireless communications interface 1496 (which may each have their own antennas (such as first mid-range antenna 1479, second mid-range antenna 1489, or third mid-range antenna 1498) or may share antenna structures with other wireless communications interfaces, as needed). The mid-range wireless communications interfaces may provide a mechanism by which the first portion 1470, the second portion 1480, and the third portion 1490 of the control logic 1406 may communicate with one another. Such mid-range wireless communications interfaces may be provided, for example, via a Bluetooth or WiFi connection, which may have ranges on the order of 10 to 30 feet (for Bluetooth) or up to several hundred feet (for WiFi).

It is to be understood that in implementations in which mid-range wireless communications interfaces are used, the mid-range wireless communications interfaces may be included in only a subset of the devices in the system. For example, the adhesive patch 1402 and the mobile communications device 1408 may include the first mid-range wireless communications interface 1477 and the third mid-range wireless communications interface 1496, but the SMDA 1404 may not include the second mid-range wireless communications interface 1487. The first portion 1470 of the adhesive patch 1402 may, however, relay information received from the SMDA 1404 via a communications connection established between the first short-range wireless communications interface 1476 and the second short-range wireless communications interface 1486 to the mobile communications device 1408 in order to communicatively connect the SMDA 1404 to the mobile communications device 1408. The table below lists some of the various implementations that may be used in order to provide communications between the first portion 1470, the second portion 1480, and the third portion 1490 of implementations involving a mobile communications device 1408; this table is not an exhaustive list, and it is to be recognized that each device listed also may include wireless communications interfaces other than those listed. For example, it is common for smartphones to include Bluetooth, WiFi, and NFC communications interfaces.

| Implementation # | Adhesive Patch | SMDA | Mobile Communications Device* |
|---|---|---|---|
| 1 | First short-range wireless communications interface | Second short-range wireless communications interface | Third short-range wireless communications interface |
| 2 | First short-range wireless communications interface + first mid-range wireless communications interface | Second short-range wireless communications interface + second mid-range wireless communications interface | Third mid-range wireless communications interface |
| 3 | First short-range wireless communications interface | Second short-range wireless communications interface + second mid-range wireless communications interface | Third mid-range wireless communications interface |
| 4 | First short-range wireless communications interface + first mid-range wireless communications interface | Second short-range wireless communications interface | Third mid-range wireless communications interface |

*The mobile communications device, may, in addition to the listed communications interfaces, also include a long-range wireless communications interface, such as an LTE, 3 G, or other type of connection that provides internet connectivity over a cellular phone connection.

In the first implementation listed in the table above, the adhesive patch 1402, the SMDA 1404, and the mobile communications device 1408 may all include short-range wireless communications interfaces and may all communicate with one another via such short-range wireless communications interfaces. This may, however, require that the mobile communications device 1408 be actively brought into close proximity to the adhesive patch 1402 and/or the SMDA 1404 due to the short range of the short-range wireless communications interfaces used. While the SMDA 1404 and the adhesive patch 1402 will naturally be brought into close proximity to one another when the SMDA 1404 is used to inject medication through one of the openings 1420 of the adhesive patch 1402, the mobile communications device 1408 may not normally be brought into such close proximity to either the SMDA 1404 or the adhesive patch 1402 as part of the medication application procedure. As such, a separate action may need to be taken by the patient (or another assisting the patient) in order to bring the mobile communications device 1408 into range of the SMDA 1404 and/or the adhesive patch 1402. While this may not be the most user-friendly approach, it is to be understood that this is still an implementation that is within the scope of this disclosure. In such an implementation, the adhesive patch 1402 and the SMDA 1404 may not include mid-range wireless communications interfaces.

In some implementations, the first implementation listed in the table above may, in contrast to the general observation provided above, be very user-friendly. For example, if the mobile communications device is a smartwatch or other wrist-wearable device, then the mobile communications device, the SMDA, and the adhesive patch may actually all be quite close to each other when a medication injection is being delivered, especially if the mobile communications device is worn on the wrist of the hand used to manipulate the SMDA. In such implementations, at the time of injection, all three elements of the system—the mobile communications device, the adhesive patch, and the SMDA—may be within a few inches of each other (or at least within a few inches of at least one of the other elements). For example, the SMDA may be within 2-4 inches of a wrist-worn mobile communications device worn by the person performing the injection as well as within 2-4 inches of the adhesive patch. In such implementations, the wrist-worn mobile communications device may be within 4-8 inches of the SMDA. If such a distance exceeds the range of the short-range wireless communications device, communication between the adhesive patch and the mobile communications device may be provided by using the SMDA as a relay between the two devices.

In the second implementation listed in the table above, the adhesive patch 1402 and the SMDA 1404 may both include both short-range wireless communications interfaces as well as mid-range wireless communications interfaces, and the mobile communications device 1408 may include a mid-range wireless communications interface. In such implementations, the short-range wireless communications interfaces in the adhesive patch 1402 and the SMDA 1404 may be used to verify that the SMDA 1404 and the adhesive patch 1402 are in close physical proximity to one another in order to potentially disengage the safety interlock 1410 in the SMDA 1404, but the mid-range wireless communications interfaces may be used for general communications between the SMDA 1404, the adhesive patch 1402, and the mobile communications device 1408.

In the third and fourth implementations listed in the table above, the adhesive patch 1402 and the SMDA 1404 may both include short-range wireless communications interfaces, and one of these two devices may also include a mid-range wireless communications interface. The mobile communications device 1408 also may include a mid-range wireless communications interface. Such implementations may function in a manner similar to the second implementation listed in the table above, except that whichever of the adhesive patch 1402 and the SMDA 1404 includes the mid-range wireless communications interface may act as a relay between the mobile communications device 1408 and whichever of the adhesive patch 1402 and the SMDA 1404 does not have the mid-range wireless communications interface.

The third processor 1492 and the third memory 1494 of the mobile communications device 1408 may be operatively connected to one another as well as to the third short range wireless communications interface 1496 and/or the third mid-range wireless communications interface, if used, and to a first long-range wireless communications interface 1495. The first long-range wireless communications interface 1495 may, for example, be a cellular data connection such as a Long-Term Evolution (LTE) or third-generation (3G) connection, and may utilize a long-range antenna 1499. In some mobile communications devices, such a first long-range wireless communications interface may be augmented or replaced by a mid-range wireless communications interface, such as a WiFi interface that allows for access to the Internet via a WiFi hotspot.

The inclusion of a mobile communications device 1408 in the system 1400 may allow for additional functionality to be provided in the system. For example, the first long-range wireless communications interface 1495 of the mobile communications device 1408 may be used by the control logic 1406 to connect to a remote server 1464 and to transmit data to the remote server 1464, which may store such data in a remote storage. Such data may include, for example, data regarding each time the control logic 1406 determines that an SMDA 1404 has been used to dispense medication. The communications connection to the remote server 1464 may be by way of a cellular data connection with a cellular service provider 1460 that provides connectivity to the Internet 1462 or other wide-area network. The remote server 1464 may, for example, be accessible by the patient's physician 1468 or, in some cases, by the medication manufacturer or distributor 1466 via the Internet 1462 (or via another connection). The data regarding medication dispensation may be used by the physician or the manufacturer/distributor to determine whether or not the patient is adhering to a prescribed medication treatment plan for the medication.

The first long-range wireless communications interface 1495 may also serve as a conduit to allow modifications to be made to the control logic 1406 from the remote server 1464. For example, if the control logic 1406 is configured to monitor the duration since the most recent administration of the medication and to prevent disengagement of the safety interlock 1410 when further medication application is attempted before the minimum amount of time has elapsed since the most recent medication application, then the control logic 1406 may be reconfigured, via instructions sent to the control logic 1406 by the remote server 1464, to utilize a different minimum allowable amount of time between medication injections via the first long-range wireless communications interface 1495. This may allow the patient's physician 1468 to alter various aspects of the medication treatment regimen for the patient remotely.

The first long-range wireless communications interface 1495 may also serve to allow for real-time or near-real-time physician involvement in association with medication delivery attempts using the SMDA 1404. For example, if repeated attempts are made to utilize an SMDA 1404 and these attempts do not result in disengagement of the safety interlock 1410, then this may be indicative of any of several potential scenarios, including, for example, a malfunction in the system 1400, a possibility that the patient does not understand the treatment regimen, a possibility that the patient is in distress, a possibility that the patient is deliberately attempting to misuse the medication, a possibility that an unauthorized user is attempting to use the medication, etc. In such scenarios, the information transmitted to the remote server 1464 via the first long-range wireless communications interface 1495 from the control logic 1406 may be analyzed to determine if the data indicates such potential scenarios, and, if so, any of several responses may be initiated. For example, in some implementations, the remote server 1464 may alert the physician 1468 or the physician's office so that the physician 1468 or someone associated with the physician 1468 can contact the patient, e.g., via cell phone (which may be the same device as the mobile communications device 1408). In some such implementations, such contact may be in the form of a video chat session or "virtual consult" in which the physician 1468 or other caregiver and the patient may be able to see each other and converse.

In some implementations, the control logic 1406 may be configured to initiate a "virtual consult" when a patient is attempting to perform a self-injection, as determined by the control logic 1406, in circumstances where the control logic determines that an abnormal physiological condition exists, such as may be indicated by various sensors included in the adhesive patch 1402 or otherwise in communication with the control logic 1406. In order to detect such physiological conditions, the system may include one or more sensors such as body temperature sensors, electrocardiogram sensors, oxygen saturation sensors, bioimpedance sensors, electroencephalographic sensors, electromyographic sensors, heart rate sensors, heart rate variability sensors, respiratory rate sensors, and blood glucose sensors. Such an abnormal physiological condition may indicate an elevated risk to the patient were they to take the medication, so a virtual consult may allow the caregiver to evaluate the nature of such a risk.

It is to be understood that reference to "sensors" herein is used in the sense that the term is generally used in the medical industry. Such sensors may generally include sensing elements that may provide some form of feedback regarding some aspect of the patient's body or physiological state, as well as, in many cases, some form of processor or circuit that acts to translate such feedback into a parameter that carries useful meaning to a monitoring physician or caregiver. For example, some temperature sensors may take the form of a thermocouple where the thermocouple generates a voltage that is generally linearly proportional to measured temperature (at least, over the small temperature range typically observed in the human body); such sensors may be require little, if any, processing in order to extract temperature data from them. In other examples, a particular sensor may involve significant processing of the signals obtained from the sensing elements in order to produce the data that the sensor is intended to measure. For example, a photoplethysmographic sensor may utilize photodetector light-sensing elements that provide detected light intensity values to a processor or circuit that then calculates a person's heart rate from the light intensity data. It is to be understood that reference to "sensors" of various types herein generally refers to whatever sensing elements are used by the sensor as well as, if present, any circuitry or processor, as well as computer-executable instructions for controlling such hardware, that may operate on signals or data produced by such sensing elements in order to provide useful physiological data. As such, reference to particular sensor types may be by way of a commonly-accepted name within the industry, and it is to be understood that such a sensor may include the various sensing elements and processing elements that are typically included in such sensors. It is also to be understood that some sensors may share one or more sensor elements and/or one or more processing elements, e.g., a heart rate sensor may utilize the same photodetector element(s) as a blood oxygen sensor, and the same processor may provide for measurements of both physiological parameters.

For example, if a patient has recently been engaging in strenuous exercise, then a perspiration or heart rate sensor that may be included in the adhesive patch 1402 may provide data indicative of an elevated heart rate or other physiological abnormality. Such information may also, for example, be obtained from another device, such as a wrist-wearable fitness tracking device, if such a device is in communication with the control logic 1406. Many commercially-available fitness devices on the market today include, for example, optical or EKG-based heart-rate sensors and also include the ability to communicate with a smartphone. Such fitness devices may thus be easily integrated into the system and used as a source for data or information that may affect the circumstances under which the control logic 1406 disengages the safety interlock 1410 and/or initiates a "virtual consult" with the patient's physician or other caregiver.

In some such implementations, the control logic 1406 may be configured to delay disengagement of the safety interlock 1410 until after the patient and their caregiver have engaged in a virtual consult. In some further such implementations, the control logic 1406 may require receipt of a release signal issued by the caregiver prior to disengaging the safety interlock 1410.

Figure 13:
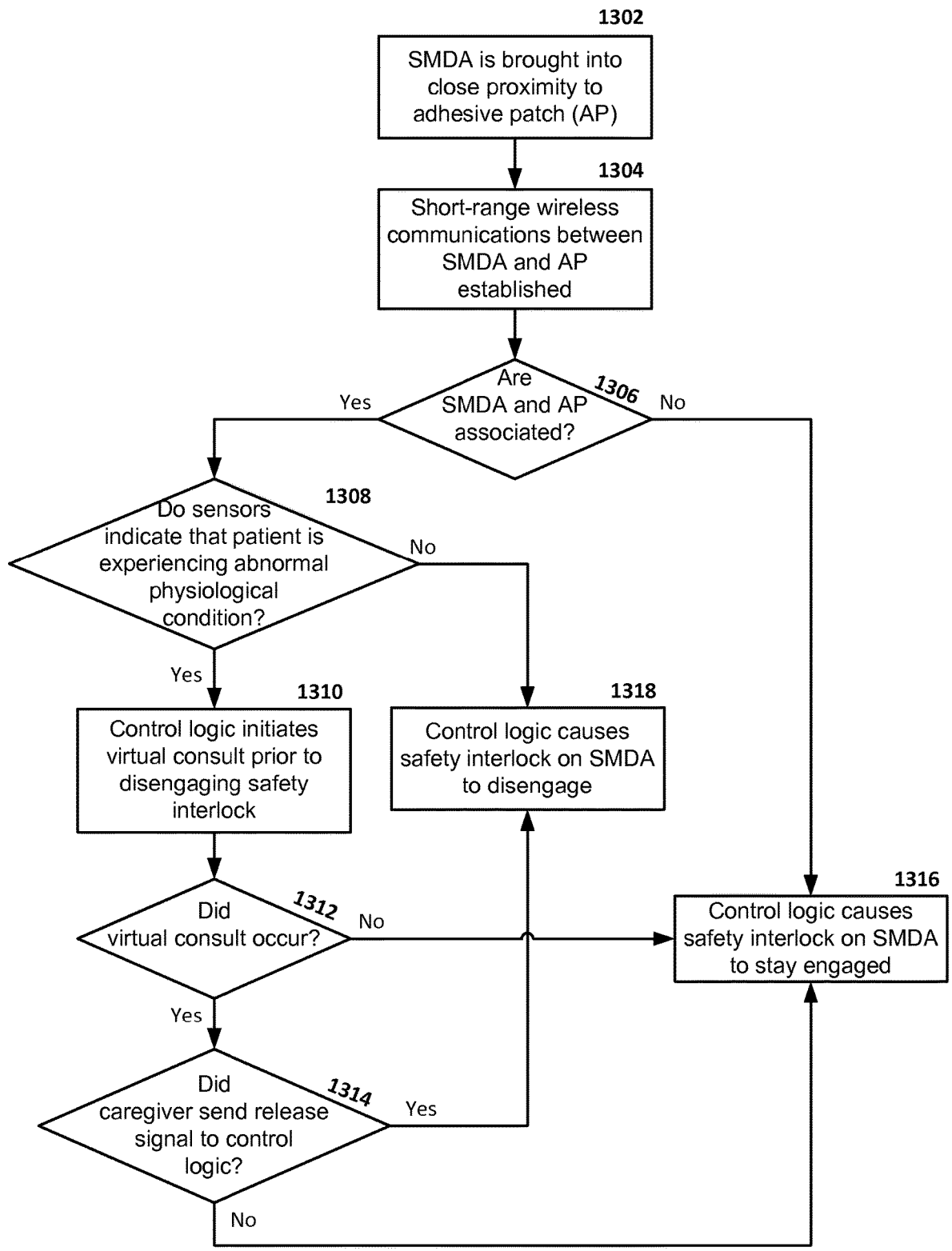
FIG. 13 depicts an example technique for initiating a virtual consultation for a patient in response to an attempt to perform a self-injection by a patient.

FIG. 13 depicts an example technique for initiating a virtual consultation for a patient in response to an attempt to perform a self-injection by a patient. The technique may begin in block 1302, in which an SMDA is brought into close enough proximity to an adhesive patch that a short range wireless communications connection between the adhesive patch and the SMDA may be established via the short-range wireless communications interfaces of the two devices in block 1304. After such a communications connection is established, the technique may proceed to block 1306, in which the control logic for the system may determine if the SMDA and the adhesive patch are associated with one another. If not, then the technique may proceed to block 1316, where the control logic may prevent disengagement of a safety interlock of the SMDA. However, if the control logic determines that there is an association between the SMDA and the adhesive patch in block 1306, then the control logic may proceed to block 1308, in which the control logic may determine whether a sensor or sensors of the system, such as may be included in the adhesive patch, may indicate that the patient is experiencing an abnormal physiological condition. If not, then the control logic may proceed to block 1318 and cause the safety interlock of an SMDA to disengage in order to allow the injection to occur. If so, however, then the control logic may initiate a virtual consult with the patient's physician in block 1310. In block 1312, the control logic may determine if the virtual consult occurred—if not, then the technique may proceed to block 1316 and the safety interlock may remain engaged. If the control logic determines in block 1312 that the virtual consult did occur, then the technique may proceed to block 1314, in which the control logic may determine whether the system has received a release signal in association with the virtual consult, such as may be sent by a doctor or nurse participating in the virtual consult. If so, then the technique may proceed to block 1318 and the safety interlock may be disengaged by the control logic. If not, then the technique may proceed to block 1316 and the safety interlock may be kept in an engaged state.

It is to be understood that in implementations in which a mobile communications device 1408 is used, the functionality provided by the long-range wireless communications interface may also be provided via a mid-range wireless communications interface as well—for example, a WiFi connection may be established between the mobile communications device 1408 and a local WiFi hotspot that provides Internet connectivity. Such implementations are also considered to be within the scope of this disclosure.

It is also to be understood that the association between an SMDA and an adhesive patch may be created on-demand with the involvement of some form of central verification service that is accessible over the Internet (or other long-range communications system). For example, each SMDA and adhesive patch that is manufactured or distributed by a particular entity may be equipped with a unique serial number. These serial numbers may be provided to the central verification service, along with information identifying the patient. The central verification service may then compare the patient identity and the serial numbers against information entered into the central verification system by, for example, the prescribing physician or a pharmacist that fulfills the prescription. This information may, for example, include a listing of each serial number of devices that the physician (or, more likely, the pharmacist) has identified as having been prescribed for the patient. Alternatively, the serial numbers may be correlated with records indicating a particular type and dosage of medication that is associated with various serial numbers, for example, the type and amount of medication that is pre-loaded into a particular SMDA. This information may then be compared against the medication type and dosage prescribed for the identified patient by their physician—if the type and dosage of the medication associated with those serial numbers match the type and dosage of the medication that is indicated as having been prescribed for the identified patient, then the serial numbers identifying the medications may be associated by the central verification service with the serial numbers of the adhesive patches that have also been provided to the central verification service in association with the patient.

It is also to be understood that for SMDAs that are cartridge-based—in other words, SMDAs where the medication can be removed from the SMDA and then replaced with new medication without requiring a new SMDA device—the association between the adhesive patch and the SMDA may, more technically, be an association between the adhesive patch and the cartridge that is presently loaded in the SMDA. In some such implementations, the second portion (including the second memory and the second processor) may be part of the medication cartridge instead of the remainder of the SMDA, although in other such implementations, the non-cartridge portion of the SMDA may still retain the second portion (including the second processor and second memory). In the latter case, each cartridge may be equipped with a different unique identifier, such as a serial number that is electronically encoded in a component of the cartridge, that is read by the SMDA when the cartridge is loaded into the SMDA. The SMDA may thus "inherit" the identity of whatever cartridge is currently loaded into the SMDA, and any decisions as to whether or not to disengage a safety interlock (or perform other actions), as discussed above, may be made on the basis of that inherited identity.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof, which may be referred to herein as "logic" or "control logic." It is to be further understood that control logic may be distributed across multiple devices, in which case reference may be made to portions of the control logic that are associated with each such device; the portions may, in aggregate, work together to provide the functionality of the control logic. Such implementations may also refer to such portions of the control logic as first, second, etc. control logics that may, in aggregate, work together to provide the functionality of the "control logic" as a whole, which may, in some instances, be referred to as an "aggregate control logic." Implementations of the subject matter described in this specification also can be implemented as one or more computer programs, i.e., one or more modules of computer program instructions, encoded on a computer storage media for execution by, or to control the operation of, data processing apparatus.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A system comprising:
    an adhesive patch, wherein the adhesive patch comprises:
        a flexible substrate having an adhesive backing for adhering the flexible substrate to a person's skin, the flexible substrate having one or more openings, each opening indicating a post-adhesion, designated injection site for subcutaneous medication delivery when the adhesive patch is adhered to the person's skin, and
        a first short-range wireless communications interface, and wherein the adhesive patch is configured to short-circuit itself upon removal from the person's skin;
    a first subcutaneous medication delivery applicator (SMDA), wherein the first SMDA includes:
        a mechanism configured to subcutaneously deliver an amount of medication through the person's skin,
        a second short-range wireless communications interface configured to receive and transmit information from and to, respectively, at least the first short-range wireless communications interface, and
        a safety interlock that prevents the mechanism from dispensing the medication when the safety interlock is engaged and that allows the mechanism to dispense the medication when disengaged; and
    control logic operatively connected with the first short-range wireless communications interface, the second short-range wireless communications interface, and the safety interlock, wherein:
        the control logic includes a first portion that is included in the adhesive patch and a second portion that is included in the first SMDA,
        the first portion of the control logic and the second portion of the control logic are configured to communicate with each other via the first short-range wireless communications interface and the second short-range wireless communications interface, respectively, and
        the control logic is configured to:
            determine whether subcutaneous injection of the medication from the first SMDA is authorized at a first time based, at least in part, on information indicating that the first SMDA is pre-associated with identifier information that identifies the first SMDA and that is pre-associated with the adhesive patch and transmitted via the first short-range wireless communications interface, the second short-range wireless communications interface, or the first short-range wireless communications interface and the second short-range wireless communications interface, and
        cause the safety interlock to disengage responsive to a determination that the subcutaneous injection of the medication is authorized.

2. The system of claim 1, wherein the one or more openings in the flexible substrate include a plurality of openings, each opening indicated by a different distinguishing characteristic selected from the group consisting of: different colored borders around each opening, different shapes for each opening, different numbers for each opening, different letters for each opening, different symbols for each opening, and combinations thereof.

3. The system of claim 1, wherein:
    the one or more openings in the flexible substrate includes a plurality of openings, the adhesive patch further comprises a plurality of switchable visual indicators,
each of the visual indicators is positioned adjacent to a different one of the openings, and
the control logic is configured to cause one or more of the switchable visual indicators to switch to a different state to indicate one or more of the post-adhesion, designated injection sites responsive to a determination that the subcutaneous injection of the medication is authorized.

4. The system of claim 1, wherein the identifier information includes a serial number pre-associated with the first SMDA and the control logic is further configured to determine whether subcutaneous injection of the medication from the first SMDA is authorized at the first time based, at least in part, on whether the serial number pre-associated with the first SMDA matches a serial number pre-associated with the adhesive patch.

5. The system of claim 4, wherein the control logic is further configured to:
determine, based at least in part on the information, a most recent time prior to the first time that subcutaneous delivery of the medication was performed,
determine whether the amount of time between the most recent time and the first time is more than a first threshold amount of time, and
determine that the subcutaneous injection of the medication is authorized at the first time based, at least further in part, on a determination that the amount of time between the most recent time and the first time is more than the first threshold amount of time.

6. The system of claim 5, wherein the most recent time when the subcutaneous delivery was performed is determined based on a most recent occurrence or occurrences of one or more events selected from the group consisting of: a previous instance in which the safety interlock of the first SMDA was disengaged, a previous instance in which the safety interlock of another SMDA that was previously in communication with the control logic was disengaged, an indication from the first SMDA that a volume of medication contained within the first SMDA decreased, an indication from another SMDA that was previously in communication with the control logic that a volume of medication contained within the other SMDA decreased, an indication from a sensor located in the adhesive patch that the person's flesh in the vicinity of the adhesive patch changed electrical characteristics consistent with insertion of a needle into the person's flesh at that location, an indication from a sensor located in another adhesive patch that was previously in communication with the control logic that the person's flesh in the vicinity of the other adhesive patch changed electrical characteristics consistent with insertion of a needle into the person's flesh at that location, an indication from a sensor located in the first SMDA that indicates that a hypodermic needle included in the first SMDA has experienced a change in electrical characteristics consistent with contact of the hypodermic needle with the person's skin, and an indication from a sensor located in another SMDA that was previously in communication with the control logic that indicates that a hypodermic needle included in the other SMDA experienced a change in electrical characteristics consistent with contact of the hypodermic needle with the person's skin.

7. The system of claim 1, wherein:
the adhesive patch further comprises a transdermal medication dispenser,
the first portion of the control logic is also operatively connected with the transdermal medication dispenser, and
the control logic is configured to adjust a rate of transdermal medication dispensation from the transdermal medication dispenser based, at least in part, on a determination that the subcutaneous injection of the medication is authorized.

8. The system of claim 1, further comprising a mobile communications device with a third short-range wireless communications interface and a first long-range wireless communications interface, wherein the control logic:
is further operatively connected with the third short-range wireless communications interface and the first long-range wireless communications interface,
further includes a third portion that is included in the mobile communications device and that is configured to communicate with one or both of the first portion and the second portion via the third short-range wireless communications interface, and
is configured to determine whether the subcutaneous injection of the medication is authorized at the first time based, at least further in part, on further information transmitted via the third short-range wireless communications interface or the first long-range wireless communications interface.

9. The system of claim 8, wherein:
the adhesive patch further comprises one or more sensors configured to obtain physiological data regarding the person, and
the control logic is configured to:
determine that, at the first time, the physiological data indicates that the person is experiencing a medical condition that presents an elevated risk were the subcutaneous injection of the medication to be authorized, and
initiate, responsive to the determination that the physiological data indicates that the person is experiencing the medical condition that presents the elevated risk were the subcutaneous injection of the medication to be authorized, communications between the mobile communications device and a remote assistance center using the first long-range wireless communications interface.

10. The system of claim 9, wherein the one or more sensors includes one or more sensors selected from the group consisting of: a body temperature sensor, an electrocardiogram sensor, an oxygen saturation sensor, a bioimpedance sensor, an electroencephalography sensor, an electromyographic sensor, a blood glucose sensor, a heart rate sensor, a heart rate variability sensor, and a respiratory rate sensor.

11. The system of claim 1, wherein:
the adhesive patch further comprises an alert mechanism,
the alert mechanism is selected from the group consisting of a haptic feedback device and an audio speaker, and
the control logic is configured to:
determine a time at which the medication is to be administered, and
cause the alert mechanism to activate responsive to determining that the medication is to be administered to indicate that the medication is to be administered at that time.

12. The system of claim 1, wherein the control logic is further configured to track usage of the first SMDA over time and store information regarding the usage of the first SMDA in a memory.

13. The system of claim 12, further comprising a mobile communications device with a third short-range wireless communications interface and a first long-range wireless communications interface, wherein the control logic:
is further operatively connected with the third short-range wireless communications interface and the first long-range wireless communications interface,
further includes a third portion that is included in the mobile communications device and that is configured to communicate with one or both of the first portion and the second portion via the third short-range wireless communications interface, and
is configured to transmit the information regarding the usage of the SMDA to a remote storage via the first long-range wireless communications interface.

14. The system of claim 1, further comprising one or more additional SMDAs, wherein:
each additional SMDA also includes another second short-range wireless communications interface configured to receive and transmit information from and to, respectively, at least the first short-range wireless communications interface,
each additional SMDA is pre-associated with corresponding identifier information that identifies that additional SMDA and that is also pre-associated with the adhesive patch, and
the control logic is further configured to determine whether subcutaneous injection of the medication from any particular SMDA of the one or more additional SMDAs is authorized at the first time based, at least in part, on information indicating that the particular SMDA is pre-associated with the corresponding identifier information that identifies the particular SMDA and that is pre-associated with the adhesive patch and transmitted via the first short-range wireless communications interface, the second short-range wireless communications interface of the particular SMDA, or the second short-range wireless communications interface of the particular SMDA and the first short-range wireless communications interface.

15. The system of claim 1, further comprising one or more additional adhesive patches, wherein each additional adhesive patch also includes another first short-range wireless communications interface configured to receive and transmit information from and to, respectively, at least the second short-range wireless communications interface.

16. The system of claim 1, wherein the first SMDA is selected from the group consisting of: a syringe, an autoinjector syringe, and a needleless jet-injector.

17. An adhesive patch comprising:
a flexible substrate having an adhesive backing for adhering the flexible substrate to a person's skin, the flexible substrate having one or more openings, each opening indicating a post-adhesion, designated injection site for subcutaneous medication delivery when the adhesive atch is adhered to the erson's skin:
a first short-range wireless communications interface;
first control logic operatively connected with the first short-range wireless communications interface, wherein:
the first control logic is configured to:
communicate with second control logic of a first subcutaneous medication delivery applicator (SMDA) via the first short-range wireless communications interface,
determine whether subcutaneous injection of a medication associated with the first SMDA is authorized at a first time based, at least in part, on information received via the first short-range wireless communications interface, wherein the information includes identifier information that identifies the first SMDA and that indicates that the first SMDA is pre-associated with the adhesive patch, and
send a first authorization signal to the first SMDA via the first short-range wireless communications interface responsive to a determination that the subcutaneous injection of the medication is authorized; and
a transdermal medication dispenser, wherein:
the first control logic is also operatively connected with the transdermal medication dispenser, and
the first control logic is configured to adjust a rate of transdermal medication dispensation from the transdermal medication dispenser based, at least in part, on a determination that the subcutaneous injection of the medication is authorized.

18. The adhesive patch of claim 17, wherein:
the one or more openings in the flexible substrate includes a plurality of openings,
the adhesive patch further comprises a plurality of switchable visual indicators,
each of the visual indicators is positioned adjacent to a different one of the openings, and
the first control logic is configured to cause one or more of the switchable visual indicators to switch to a different state to indicate one or more of the post-adhesion, designated injection sites responsive to a determination that the subcutaneous injection of the medication is authorized.

19. The adhesive patch of claim 17, wherein the one or more openings in the flexible substrate include a plurality of openings, each opening indicated by a different distinguishing characteristic selected from the group consisting of:
different colored borders around each opening, different shapes for each opening, different numbers for each opening, different letters for each opening, different symbols for each opening, and combinations thereof.

20. The adhesive patch of claim 17, wherein the first control logic is further configured to:
store information that allows the first control logic to determine that a plurality of different SMDAs, including the first SMDA, are each pre-associated with the adhesive patch, and
send a corresponding authorization signal to any of the SMDAs based, at least in part, on information received from that respective SMDA via the first short-range wireless communications interface when the information received from that SMDA indicates that that SMDA is pre-associated with the adhesive patch.

21. The adhesive patch of claim 20, wherein the information that allows the first control logic to determine that the plurality of different SMDAs, including the first SMDA, are pre-associated with the adhesive patch includes information identifying SMDAs from at least two different medication manufacturers or at least two different SMDA manufacturers.

22. The adhesive patch of claim 20, wherein the first control logic is further configured to:
store information for each SMDA or each medication associated with each SMDA indicating the most recent time that medication or that SMDA was used,
determine, prior to sending the corresponding authorization signal for any of the SMDAs, whether the amount of time between the most recent time that that medication or that SMDA was used and a current time is more than a threshold amount of time associated with that medication or that SMDA, and determine that the subcutaneous injection of that medication or the medication associated with that SMDA is authorized based, at least further in part, on a determination that the amount of time between the most recent time that that medication or that SMDA was used and the current time is more than the threshold amount of time associated with that medication or that SMDA.

23. The adhesive patch of claim 17, wherein the identifier information includes a serial number pre-associated with the first SMDA and the first control logic is further configured to determine whether subcutaneous injection of the medication from the first SMDA is authorized at the first time based, at least in part, on whether the serial number pre-associated with the first SMDA matches a serial number pre-associated with the adhesive patch.

24. The adhesive patch of claim 23, wherein the first control logic is further configured to:

determine, based at least in part on the information, the most recent time prior to the first time that subcutaneous delivery of the medication was performed, determine whether the amount of time between the most recent time and the first time is more than a first threshold amount of time, and determine that the subcutaneous injection of the medication is authorized at the first time based, at least further in part, on a determination that the amount of time between the most recent time and the first time is more than the first threshold amount of time.

25. A system comprising:

an adhesive patch, wherein the adhesive patch comprises:
a flexible substrate having an adhesive backing for adhering the flexible substrate to a person's skin, the flexible substrate having one or more openings, each opening indicating a post-adhesion, designated injection site for subcutaneous medication delivery when the adhesive patch is adhered to the person's skin,
a first short-range wireless communications interface, and
a transdermal medication dispenser;

a first subcutaneous medication delivery applicator (SMDA), wherein the first SMDA includes:
a mechanism configured to subcutaneously deliver an amount of medication through the person's skin,
a second short-range wireless communications interface configured to receive and transmit information from and to, respectively, at least the first short-range wireless communications interface, and
a safety interlock that prevents the mechanism from dispensing the medication when the safety interlock is engaged and that allows the mechanism to dispense the medication when disengaged; and control logic operatively connected with the first short-range wireless communications interface, the second short-range wireless communications interface, and the safety interlock, wherein:

the control logic includes a first portion that is included in the adhesive patch and a second portion that is included in the first SMDA, the first portion of the control logic and the second portion of the control logic are configured to communicate with each other via the first short-range wireless communications interface and the second short-range wireless communications interface, respectively, the first portion of the control logic is operatively connected with the transdermal medication dispenser, and the control logic is configured to:
determine whether subcutaneous injection of the medication from the first SMDA is authorized at a first time based, at least in part, on information indicating that the first SMDA is pre-associated with identifier information that identifies the first SMDA and that is pre-associated with the adhesive patch and transmitted via the first short-range wireless communications interface, the second short-range wireless communications interface, or the first short-range wireless communications interface and the second short-range wireless communications interface, cause the safety interlock to disengage responsive to a determination that the subcutaneous injection of the medication is authorized, and adjust a rate of transdermal medication dispensation from the transdermal medication dispenser based, at least in part, on a determination that the subcutaneous injection of the medication is authorized.

26. The system of claim 25, wherein the first SMDA is selected from the group consisting of: a syringe, an autoinjector syringe, and a needleless jet-injector.

27. The system of claim 25, wherein the adhesive patch is configured to short-circuit itself upon removal from the person's skin.

28. The system of claim 25, wherein the identifier information includes a serial number pre-associated with the first SMDA and the control logic is further configured to determine whether subcutaneous injection of the medication from the first SMDA is authorized at the first time based, at least in part, on whether the serial number pre-associated with the first SMDA matches a serial number pre-associated with the adhesive patch.

29. The system of claim 25, wherein the control logic is further configured to track usage of the first SMDA over time and store information regarding the usage of the first SMDA in a memory.

30. The system of claim 25, further comprising one or more additional adhesive patches, wherein each additional adhesive patch also includes another first short-range wireless communications interface configured to receive and transmit information from and to, respectively, at least the second short-range wireless communications interface.

* * * * *